United States Patent
Totani et al.

(10) Patent No.: US 11,884,907 B2
(45) Date of Patent: Jan. 30, 2024

(54) CULTURE CONTAINER, METHOD FOR CULTURING LYMPHOCYTES, CULTURE-CONTAINER PRODUCTION METHOD, AND SOLID-PHASING APPARATUS

(71) Applicant: TOYO SEIKAN GROUP HOLDINGS, LTD., Tokyo (JP)

(72) Inventors: Takahiko Totani, Kanagawa (JP); Satoshi Tanaka, Kanagawa (JP); Takeshi Aihara, Kanagawa (JP); Yoichi Ishizaki, Kanagawa (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 1161 days.

(21) Appl. No.: 15/184,649

(22) Filed: Jun. 16, 2016

(65) Prior Publication Data
US 2016/0289624 A1    Oct. 6, 2016

Related U.S. Application Data

(63) Continuation of application No. PCT/JP2014/006252, filed on Dec. 16, 2014.

(30) Foreign Application Priority Data

Dec. 18, 2013  (JP) ................................ 2013-261181
Dec. 25, 2013  (JP) ................................ 2013-267082

(51) Int. Cl.
| C12M 1/12 | (2006.01) |
| C12N 5/0783 | (2010.01) |
| C12M 1/00 | (2006.01) |
| C12M 1/04 | (2006.01) |

(52) U.S. Cl.
CPC ............ *C12M 25/00* (2013.01); *C12M 23/14* (2013.01); *C12M 23/20* (2013.01); *C12M 23/24* (2013.01); *C12M 25/06* (2013.01); *C12N 5/0636* (2013.01); *C12N 2501/515* (2013.01); *C12N 2513/00* (2013.01); *C12N 2533/52* (2013.01); *C12N 2533/54* (2013.01)

(58) Field of Classification Search
None
See application file for complete search history.

(56) References Cited

U.S. PATENT DOCUMENTS

| 9,441,193 B2 | 9/2016 | Tanaka et al. |
| 9,925,220 B2 * | 3/2018 | Zhang .................... A61P 31/00 |
| 2007/0243634 A1 | 10/2007 | Pamula et al. |
| 2009/0258417 A1 | 10/2009 | Tanaka et al. |
| 2010/0068764 A1 | 3/2010 | Sista et al. |
| 2010/0075406 A1 | 3/2010 | Tanaka et al. |
| 2013/0115690 A1 | 5/2013 | Nakajima et al. |

FOREIGN PATENT DOCUMENTS

| CN | 1419597 A | | 5/2003 |
| CN | 1905905 A | | 1/2007 |
| CN | 101302491 A | | 11/2008 |
| CN | 101326279 A | | 12/2008 |
| CN | 101472940 A | | 7/2009 |
| CN | 101668843 A | | 3/2010 |
| CN | 102985526 A | | 3/2013 |
| JP | 2007175028 A | | 7/2007 |
| JP | 2009055894 A | | 3/2009 |
| JP | 2009195228 A | | 9/2009 |
| JP | 4399710 B2 | | 1/2010 |
| WO | 01/62895 A2 | | 8/2001 |
| WO | 2005/030273 A2 | | 4/2005 |
| WO | 2007/120241 A2 | | 10/2007 |
| WO | 2007136386 A2 | | 11/2007 |
| WO | 2008023771 A1 | | 2/2008 |
| WO | WO 2008138214 | * | 11/2008 |
| WO | WO2011052638 | * | 5/2011 |

OTHER PUBLICATIONS

Partial Supplementary European Search Report issued in European Patent Application No. 14871598.0 dated Jun. 26, 2017 (10 pages).
Office Action issued in corresponding Chinese Application No. 201480057477.1 dated Dec. 5, 2016 (10 pages).
International Search Report issued in the corresponding International Application No. PCT/JP2014/006252, dated Mar. 24, 2015 (4 pages).
International Preliminary Report on Patentability and Written Opinion issued in the corresponding International Application No. PCT/JP2014/006252, dated Jun. 30, 2016 (7 pages).
Yannelli et al.; "Use of anti-CD3 monoclonal antibody in the generation of effector cells from human solid tumors for use in cancer biotherapy"; Journal of Immunological Methods, vol. 130, No. 1, p. 91-100 (1990) (10 pages).
Yano et al.; "Characterization of Liquid Surfaces Using the Advanced Surface-Horizontal X-ray Reflectometer at SPring-8"; Bunseki Kagaku, vol. 59, No. 6; pp. 437-445 (2010) (9 pages).
Office Action issued in corresponding Chinese Application No. 201710264731.0; dated Aug. 20, 2019 (17 pages).

* cited by examiner

*Primary Examiner* — Michail A Belyavskyi
(74) *Attorney, Agent, or Firm* — Osha Bergman Watanabe & Burton LLP

(57) ABSTRACT

A culture container for culturing lymphocytes includes an immobilized surface and a non-immobilized surface, wherein the culture container is formed of a gas permeable film, the immobilized surface and the non-immobilized surface are container inner surfaces facing each other, and anti-CD3 antibodies are immobilized in the immobilized surface at a concentration of 10 to 300 ng/cm².

1 Claim, 16 Drawing Sheets

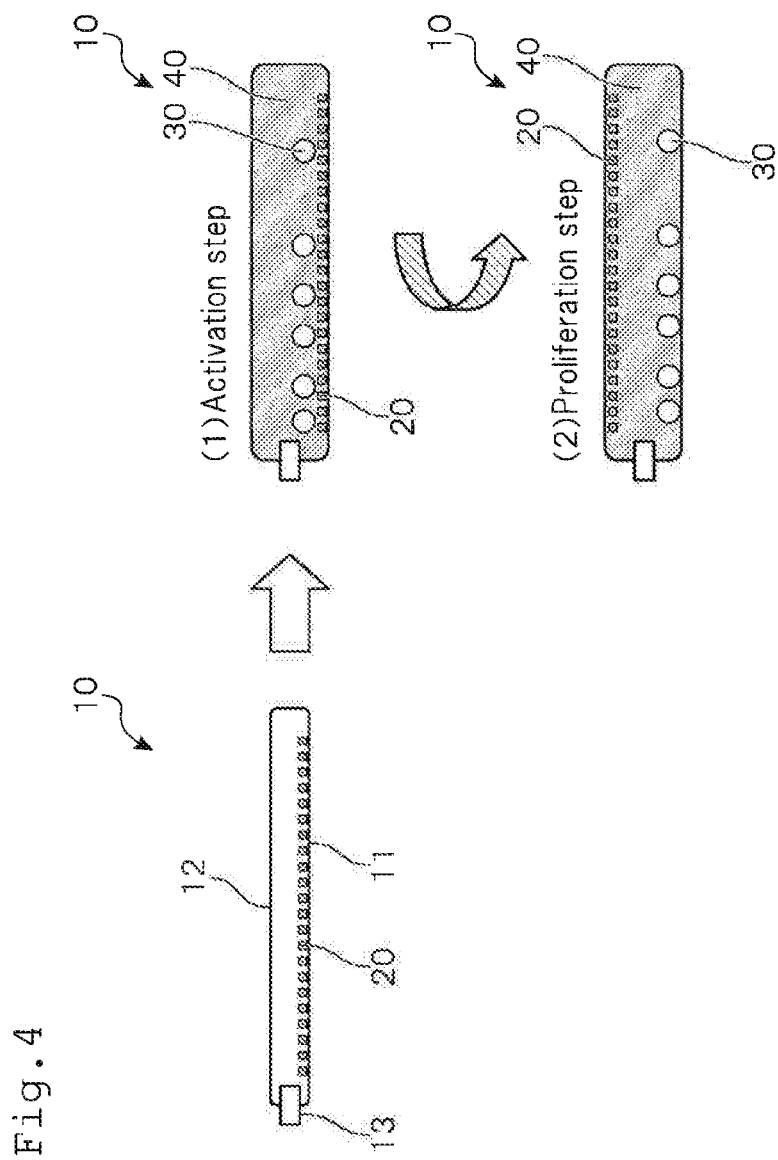

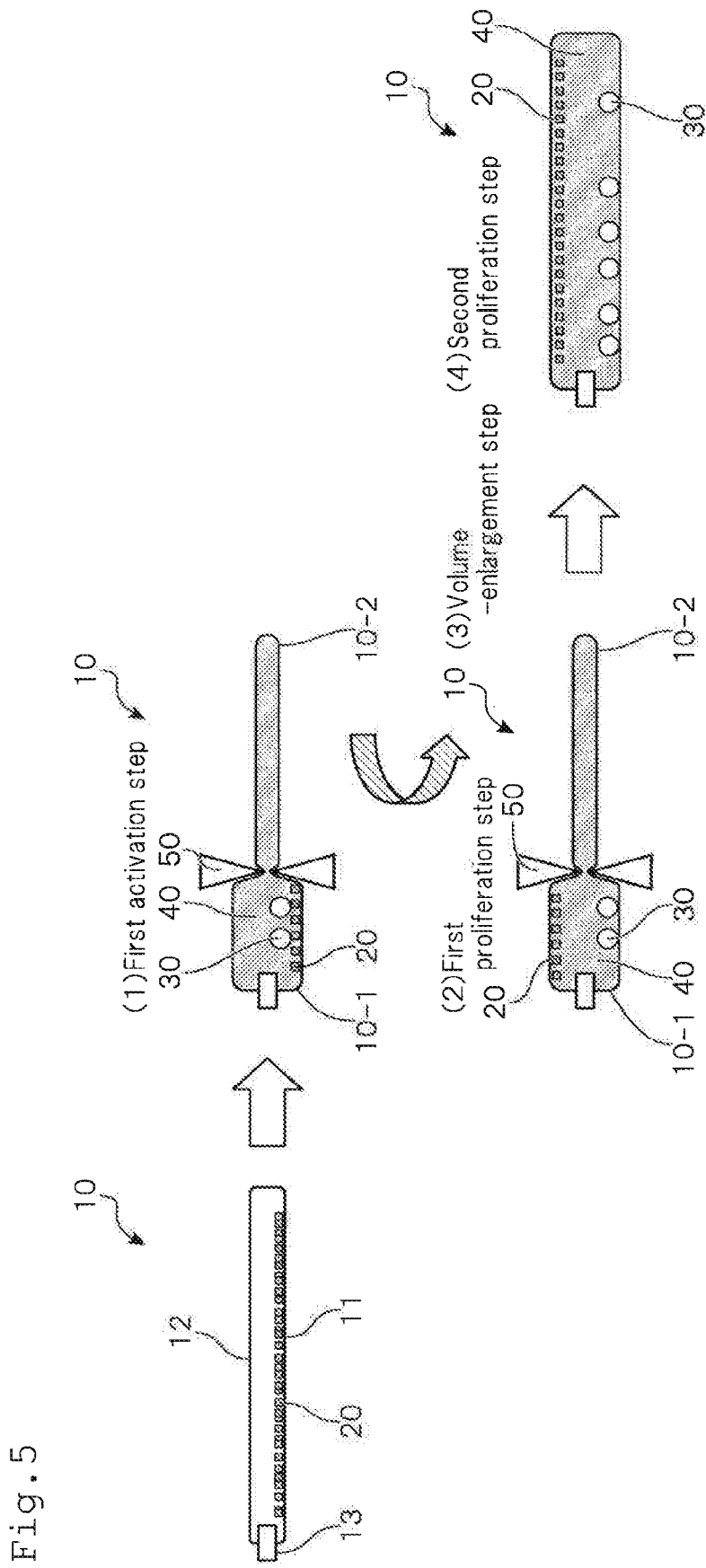

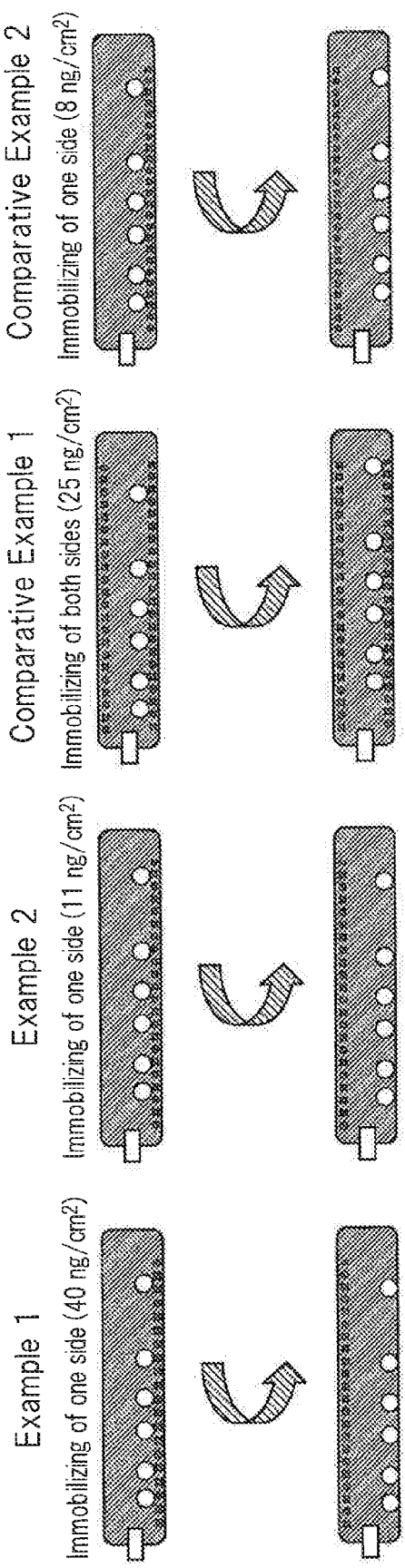

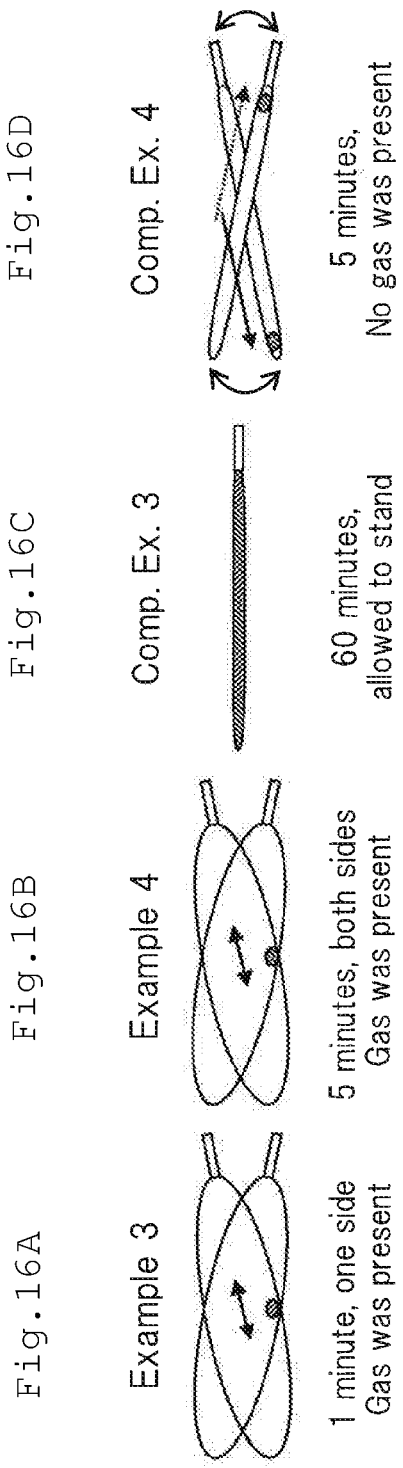
Fig.16A Example 3 — 1 minute, one side Gas was present
Fig.16B Example 4 — 5 minutes, both sides Gas was present
Fig.16C Comp. Ex. 3 — 60 minutes, allowed to stand
Fig.16D Comp. Ex. 4 — 5 minutes, No gas was present
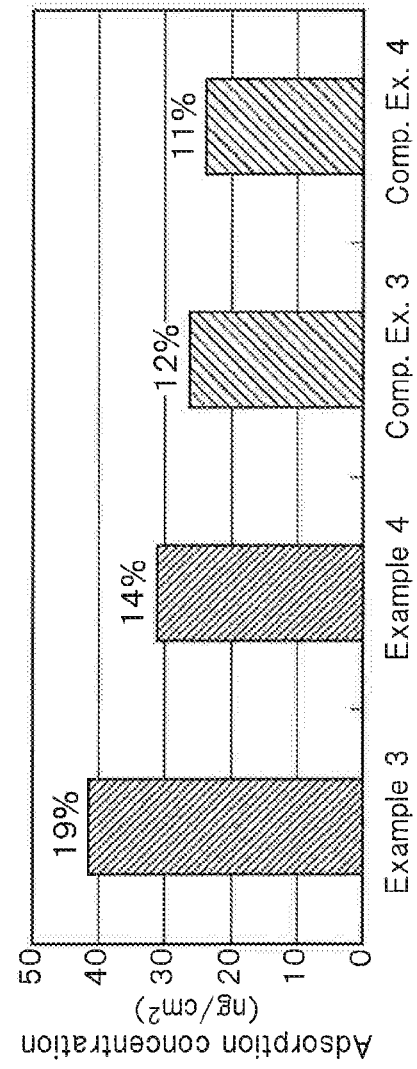
Fig.17

Example 5

5 minutes

Comp. Ex. 5

60 minutes

Comp. Ex. 6

5 minutes

Example 6

1 minute

Comp. Ex. 7

60 minutes

CULTURE CONTAINER, METHOD FOR CULTURING LYMPHOCYTES, CULTURE-CONTAINER PRODUCTION METHOD, AND SOLID-PHASING APPARATUS

TECHNICAL FIELD

The present invention relates to a cell culture technology. In particular, the present invention relates to a culture container, a method for culturing lymphocytes, a method for producing a culture container in which proteins are immobilized and an immobilizing apparatus.

BACKGROUND ART

In recent years, in the fields of pharmaceuticals production, gene therapy, regenerative therapy, immune therapy or the like, there has been a demand for culturing a large amount of cells, tissues, microorganisms efficiently in an artificial environment.

Under such circumstances, culture of a large amount of cells in a closed system by sealing cells and a culture liquid in a culture bag formed of a gas-permeable film has been conducted.

In the meantime, in order to proliferate lymphocytes, it is required to activate lymphocytes at first. Therefore, lymphocytes were activated on a base member to which anti-CD3 antibodies had been immobilized, and then the activated lymphocytes were sealed in a culture bag and proliferated.

At this time, as shown in FIG. 8, in general, a flask in which anti-CD3 antibodies are immobilized to the bottom surface thereof was used for activation of lymphocytes and, after activation of the lymphocytes, the activated lymphocytes were transferred to a culture bag to conduct cultivation of the lymphocytes. The reason therefor is as follows: lymphocytes have properties that, while they are required to be irritated by anti-CD3 antibodies in order to be proliferated, they become hardly be proliferated when irritated continuously by anti-CD3 antibodies. Therefore, after activation of lymphocytes, the activated lymphocytes are required to be cultured in a container where anti-CD3 antibodies are not immobilized.

As a culture container for activating lymphocytes, a closed cell culture container (disclosed in Patent Document 1) or the like can be given. In this closed cell culture container, anti-CD3 antibodies are immobilized on the entire surface of the container (paragraphs 0048 and 0057), whereby lymphocytes can be activated efficiently.

As mentioned above, activation of lymphocytes is generally conducted by anti-CD3 antibodies. That is, lymphocytes are activated in a container in which anti-CD3 antibodies are immobilized, and thereafter, the activated lymphocytes are sealed in a culture bag in which anti-CD3 antibodies are not immobilized, whereby lymphocytes are proliferated.

Therefore, prior to activation of lymphocytes, it was required to immobilize (coat) anti-CD3 antibodies in a container used for activation of lymphocytes.

As the conventional method for immobilizing, in general, after immersing the bottom surface of a flask in a solution containing anti-CD3 antibodies and allowing the flask to stand, the solution is then removed, whereby anti-CD3 antibodies are immobilized.

Specifically, for example, Patent Document 2 discloses preparation of a flask in which antibodies are immobilized, in which anti-CD3 antibodies are immersed homogenously in the bottom surface of a flask, and stored in a refrigerator overnight, and then, the anti-CD3 antibodies are withdrawn, thereby to prepare a flask in which antibodies are immobilized (paragraphs 0035 to 0036, and FIG. 1).

Further, Patent Document 1 states that a solution obtained by dissolving anti-CD3 antibodies is sealed in an accommodating part of a container, and the container is allowed to stand for a prescribed period of time, whereby the anti-CD3 antibodies are immobilized on the film surface of the container (paragraph 0015 and FIG. 1).

Patent Document 1
  JP-A-2007-175028
Patent Document 2
  Japan Patent No. 4399710

SUMMARY OF THE INVENTION

However, if lymphocytes are cultured by using only the closed cell culture container disclosed in Patent Document 1, since the lymphocytes are continued to be irritated by anti-CD3 antibodies after the activation thereof, the lymphocytes are excessively irritated, and as a result, proliferation thereof is suppressed. Accordingly, in order to culture a large amount of lymphocytes efficiently, it is desirable to use this closed cell culture container as a container dedicated for activation, and to conduct proliferation of the cells in a separate culture container.

Therefore, in this conventional technology, if a large amount of lymphocytes is efficiently cultured, it may be difficult to transfer activated cells or there may be a risk of contamination occurs.

The inventors of the present invention made intensive studies, and have developed a culture container for culturing lymphocytes, wherein one or more embodiments of the culture container are formed of a gas-permeable film, anti-CD3 antibodies are immobilized on only one of the container inner surfaces facing each other, thereby to provide an immobilizing surface and a non-immobilizing surface. The culture container is arranged such that the immobilized surface becomes a bottom surface, thereby to activate lymphocytes, and thereafter, the culture container is arranged such that the non-immobilized surface becomes a bottom surface, thereby to proliferate lymphocytes, whereby the inventors successfully enabled activation and proliferation of lymphocytes efficiently and simultaneously in a single container.

That is, one or more embodiments of the present invention provide a culture container capable of efficiently activating and proliferating lymphocytes in a single culture container, as well as a method for culturing lymphocytes.

Further, the conventional immobilizing methods described in Patent Documents 1 and 2 may require a long resting time to allow antibodies to be sufficiently immobilized.

Further, since most of antibodies remain in a solution without being adsorbed to the inside of the container, the conventional methods may require antibodies to be used in an amount larger than the amount immobilized. For example, as mentioned later, when a container in which antibodies are sealed by a conventional method is allowed to stand for 1 hour, only 10% of the antibodies were adsorbed to the inside of the container, and the remaining 90% of the antibodies were discarded without being immobilized in the container.

Meanwhile, proteins such as antibodies are easily affected by heat, and the functions thereof disappear when adsorbed at high temperatures. Therefore, antibodies are materials that are difficult to be immobilized in a container. On the other hand, it is desired that immobilizing be conducted in a required amount for a short period of time by using a small amount of proteins. Further, since antibodies are generally expensive, it is desired that the amount of antibodies being discarded wastefully be reduced.

The inventors of the present invention made intensive studies, and found that, by sealing liquid droplets of a protein solution in a container together with a gas and by moving these liquid droplets on the inner surface of the container, protein molecules concentrated in the gas-liquid interface of the liquid droplets are efficiently adsorbed in the container. One or more embodiments of the present invention have been completed based on this finding.

That is, one or more embodiments of the present invention is aimed at providing, when immobilizing proteins to the inner surface of a container, a method for efficiently immobilizing proteins in a container by sealing liquid droplets of a protein solution in the container together with a gas, and by moving the liquid droplets on the inner surface of the container, thereby allowing the proteins to be immobilized in the container efficiently, as well as a immobilizing apparatus for implementing this method.

According to one or more embodiments of the present invention, the culture container is a culture container for culturing lymphocytes, wherein the culture container is formed of a gas-permeable film, antibodies are immobilized on only one of the container inner surfaces facing each other, thereby to provide a immobilizing surface and a non-immobilizing surface, and in the immobilized surface, anti-CD3 antibodies are immobilized at a concentration of 10 to 300 ng/cm².

According to one or more embodiments of the present invention, the method for culturing lymphocytes is a method for culturing lymphocytes using the above-mentioned culture container, comprising the steps of: an activation step in which lymphocytes and a culture liquid are sealed in the culture container, and the culture container is arranged such that the immobilized surface becomes a bottom surface, thereby to activate the lymphocytes, and a proliferation step in which the culture container is inverted upside down and arranged such that the non-immobilized surface becomes a bottom surface, thereby to proliferate the lymphocytes.

According to one or more embodiments of the present invention, the method for producing a culture container is a method for producing a culture container in which proteins are immobilized, wherein liquid droplets in which the proteins are dissolved are injected into the culture container and the liquid droplets are moved to part or the whole of the inner surface of the culture container.

Further, according to one or more embodiments of the present invention, the immobilizing apparatus is a immobilizing apparatus for allowing proteins to be immobilized on the inner surface of a culture container, comprising: a mounting table on which the liquid droplets containing the proteins being dissolved therein and a culture container are mounted, and a driving means that move the mounting table to allow the liquid droplets in the culture container to move on the inner surface of the culture container.

Advantageous Effects of the Invention

According to one or more embodiments of the present invention, it is possible to conduct activation and proliferation of lymphocytes efficiently in a single culture container without using a dedicated culture apparatus or the like.

Therefore, it becomes possible to eliminate troublesomeness in transfer conducted in order to prevent excessive irritation exerted by antibodies on lymphocytes and risk of contamination. According to one or more embodiments of the present invention, it is possible to provide a method for producing a culture container that efficiently immobilized proteins and an immobilizing apparatus for conducting this method.

BRIEF DESCRIPTION OF THE DRAWINGS

FIG. 4 is a view showing the method for culturing lymphocytes according to a first embodiment of the present invention;

FIG. 5 is a view showing the method for culturing lymphocytes according to a second embodiment of the present invention;

FIG. 6A is a schematic view showing Example 1 of the culture container and the method for culturing lymphocytes according to one or more embodiments of the present invention;

FIG. 6B is a schematic view showing Example 2 of the culture container and the method for culturing lymphocytes according to one or more embodiments of the present invention;

FIG. 6C is a schematic view showing Comparative Example 1 of the culture container and the method for culturing lymphocytes according to one or more embodiments of the present invention;

FIG. 6D is a schematic view showing Comparative Example 2 of the culture container and the method for culturing lymphocytes according to one or more embodiments of the present invention;

FIG. 16A is a schematic view showing Example 3 of the culture container (culture bag in which antibodies are immobilized) according to one or more embodiments of the present invention;

FIG. 16B is a schematic view showing Example 4 of the culture container (culture bag in which antibodies are immobilized) according to one or more embodiments of the present invention;

FIG. 16C is a schematic view showing Comparative Example 3 of the culture container (culture bag in which antibodies are immobilized) according to one or more embodiments of the present invention;

FIG. 16D is a schematic view showing Comparative Example 4 of the culture container (culture bag in which antibodies are immobilized) according to one or more embodiments of the present invention;

FIG. 17 is a graph showing the results of experiments conducted in Examples and Comparative Examples in the method for producing a culture container (culture bag in which antibodies are immobilized) according to one or more embodiments of the present invention;

MODE FOR CARRYING OUT THE INVENTION

Figure 1A:
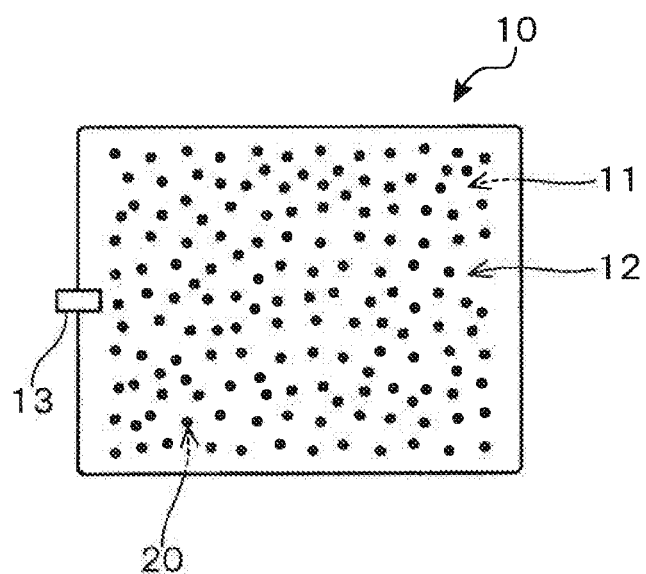
FIG. 1A is a view showing the culture container according to one or more embodiments of the present invention.
Figure 1B:
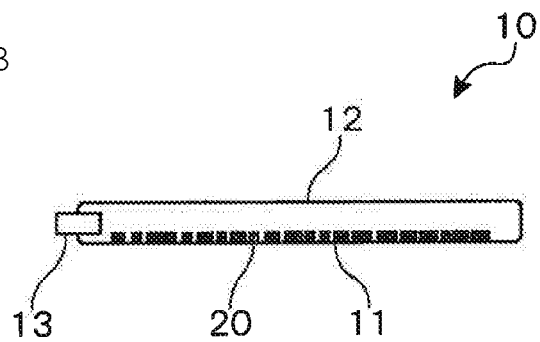
FIG. 1B is a view showing the culture container according to one or more embodiments of the present invention.

Hereinbelow, a detailed explanation will be made on one or more embodiments of the culture container and the method for culturing lymphocytes according to one or more embodiments of the present invention. First, one or more embodiments of the culture container according to the present invention will be explained with reference to FIG. 1. FIG. 1 shows a schematic view as viewed from the above and a schematic view as viewed from the side of the culture container being mounted on a mounting table (not shown).

[Culture Container]

As shown in FIG. 1, the culture container 10 according to one or more embodiments of the present invention has container walls facing with each other in a vertical direction. One of the container inner surfaces is a immobilized surface 11 (bottom surface of the container shown in FIG. 1) in which antibodies 20 are immobilized. The other of the container inner surfaces is a non-immobilized surface 12 (upper surface of the container shown in FIG. 1) in which no antibodies 20 are immobilized. The culture container 10 is provided with a tube 13. By this tube 13, sealing of lymphocytes and a culture liquid in the culture container 10 and recovery of the lymphocytes cultured and the culture liquid are conducted. In the example shown in the figure, only one tube 13 is attached to the culture container 10, but two or more tubes 13 may be attached.

The culture container 10 is formed in the shape of a bag by using a film having gas permeability required for cell culture. As the material for the culture container 10, a polyolefin resin such as polyethylene and polypropylene can be preferably used.

As the antibodies 20 to be immobilized to the immobilized surface 11, it is preferable to use anti-CD3 antibodies. Lymphocytes can be activated by anti-CD3 antibodies and proliferated.

The concentration of the antibodies 20 immobilized on the immobilized surface 11 is preferably 10 to 300 ng/cm$^2$, more preferably 10 to 40 ng/cm$^2$.

By allowing the concentration of the immobilized antibodies 20 to be 10 ng/cm$^2$ or more, lymphocytes can be effectively activated, and thereafter, the activated lymphocytes can be efficiently proliferated. If the concentration of the immobilized antibodies 20 is allowed to be larger than 40 ng/cm$^2$, no differences arise in proliferation efficiency of lymphocytes, and on the contrary, the cost of the container increases due to excessive use of antibodies.

The closed packing concentration of anti-CD3 antibodies in the immobilized surface 11 is 300 ng/cm$^2$. Within this range, it is possible to sufficiently activate lymphocytes and then proliferate the lymphocytes efficiently. On the other hand, the concentration of anti-CD3 antibodies exceeding 300 ng/cm$^2$ is not preferable, since the anti-CD3 antibodies may float in the culture liquid in the culture container 10, causing excessive irritation on the lymphocytes.

The culture container 10 according to one or more embodiments of the present invention can be produced as follows, for example.

First, low-density polyethylene is extruded by means of a plastic extrusion molding apparatus to form a film. Then, by using an impulse sealer, a bag-shaped culture container 10 is produced from this film. As shown in FIG. 1, the culture container 10 is produced such that it is provided with the tube 13.

Subsequently, the culture container 10 is mounted on a mounting table, and a prescribed amount of a gas is sealed. At that time, a buffer solution in which the antibodies 20 are dissolved is continuously sealed. By swinging or the like of the culture container 10, the liquid droplets of the buffer solution are moved on the bottom surface of the culture container 10, whereby the antibodies 20 contained in the buffer solution are adhered to the bottom surface of the culture container 10. As a result, the antibodies 20 are adhered only to the bottom surface in the culture container 10, whereby the immobilized surface 11 is formed. At this time, the upper surface of the culture container 10 is formed as a non-immobilized surface 12 on which no antibodies 20 are adhered.

Subsequently, the state of storage of the culture container 10 according to one or more embodiments of the present invention will be explained.

It is preferred that the culture container 10 be stored in a state in which the immobilized surface 11 and the non-immobilized surface 12 are not in contact with each other.

Figure 2:
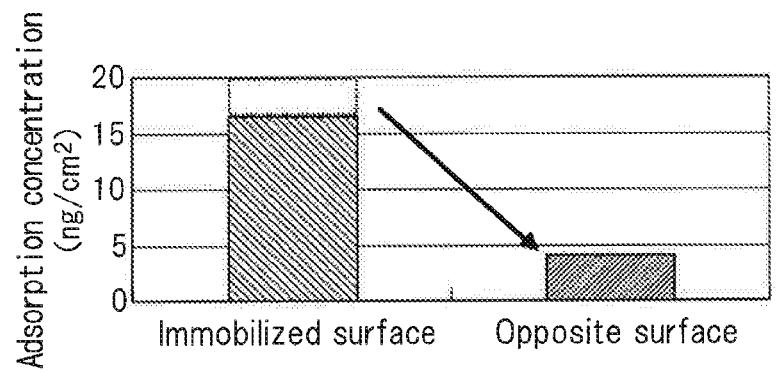
FIG. 2 is a graph showing the results of move of antibodies when storing the culture container in a state where the inner surfaces of the container are laminated.

That is, when the culture container 10 is stored at 37° C. for 2 hours under a load of 1.6 kg in a state where the immobilized surface 11 and the non-immobilized surface 12 are in contact with each other, as shown in FIG. 2, about 20% of the antibodies 20 are moved from the immobilized surface 11 to the non-immobilized surface 12. The antibodies 20 that have been moved to the non-immobilized surface 12 in this way may irritate lymphocytes excessively to lower the rate of proliferation thereof when proliferating is conducted after activation of lymphocytes. Therefore, it is preferable to suppress move of the antibodies 20 from the immobilized surface 11 to the non-immobilized surface 12 as much as possible.

When storing the culture container 10 according to one or more embodiments of the present invention, it is preferred that a prescribed amount of a gas be sealed in the culture container 10 and that a state in which the immobilized surface 11 and the non-immobilized surface 12 are not in contact with each other be maintained.

Specifically, it is preferred that the amount of a gas to be sealed be 0.01 to 4 ml per $cm^2$ of the bottom surface of the culture container 10. By allowing the amount of a gas to be sealed to be in this range, it is possible to prevent contact of the immobilized surface 11 and the non-immobilized surface 12.

Although no specific restrictions are imposed on the gas to be sealed, an inert gas is preferable, and air, nitrogen gas or the like can be used. Such gas can be injected into the culture container 10 through the tube 13 by a gas supply apparatus.

Figure 3A:
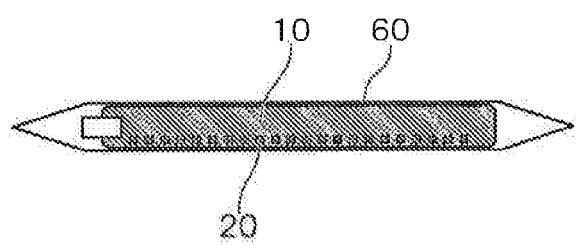
FIG. 3A is a view showing the state of storage of the culture container according to one or more embodiments of the present invention.

As the specific manner of storage of the culture container 10 according to one or more embodiments of the present invention, as shown in FIG. 3A, it is preferred that the shape of the culture container 10 be retained by an outer covering container 60 having rigidity. When the culture container 10 is stored by using such outer covering container 60, by sealing only a small amount of a gas in the culture container 10, the culture container 10 can be stored without causing movement of the antibodies 20.

Figure 3B:
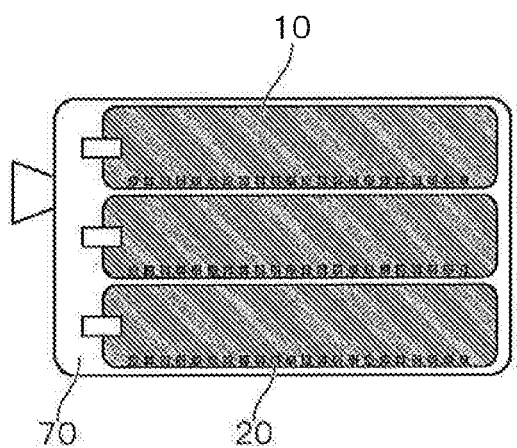
FIG. 3B is a view showing the state of storage of the culture container according to one or more embodiments of the present invention.

Further, as shown in FIG. 3B, it is preferred that the culture container 10 be stored in a state swollen with a gas and wrapped with a packaging container 70. Due to such a configuration, it is possible to package a plurality of culture containers 10 simply and store them without causing movement of the antibodies 20.

As explained hereinabove, the culture container 10 according to one or more embodiments of the present invention is made of a gas-permeable film, and the antibodies 20 are immobilized on only one surface of container inner walls facing each other, whereby it is provided with the immobilized surface 11 and the non-immobilized surface 12. The lymphocytes sealed within the culture container 10 are gathered at the bottom of the container.

Therefore, by using the culture container 10 such that the immobilized surface 11 becomes a bottom surface when activating lymphocytes and such that the non-immobilized surface 12 becomes a bottom surface when proliferating lymphocytes, excessive irritation of lymphocytes exerted by the antibodies 20 can be prevented, whereby activation and proliferation of lymphocytes can be efficiently conducted in a single container. As a result, it becomes possible to eliminate troublesomeness in transfer or risk of contamination. Further, since moving from activation to proliferation is a simple operation (i.e. only inverting the container), it can be conducted simply without using a dedicated apparatus or the like.

Further, by sealing a prescribed amount of a gas in the culture container 10 according to one or more embodiments of the present invention and retaining a state where the immobilized surface 11 and the non-immobilized surface 12 are not in contact with each other, it is possible to store the culture container 10 without lowering the effect of preventing excessive irritation on lymphocytes.

In the meantime, in a conventional flask that is used for activating lymphocytes, anti-CD3 antibodies are immobilized only on the bottom surface, and lymphocytes can be activated by this configuration. However, proliferation of lymphocytes after activation cannot be conducted by using a single flask. The reason is that, in a flask, the number of cells per area cannot be maintained at an appropriate density. Namely, lymphocytes are proliferated after activation, it is required to enlarge the culture area. In one or more embodiments, it is possible to enlarge the culture area by partitioning part of the culture container by means of a clip or a roller, and by moving, removing or the like of the clip or the roller in accordance with the proliferation of cells. However, such enlargement of the culture area cannot be conducted in a flask. A flask can be used for activating lymphocytes, but is not suited to proliferation.

Method for Culturing Lymphocytes

First Embodiment

Subsequently, a first embodiment of the method for culturing lymphocytes according to one or more embodiments of the present invention will be explained with reference to FIG. 4. As shown in FIG. 4, the method for culturing lymphocytes according to one or more embodiments of the present invention comprises the step of an activation step (1) and a proliferation step (2).

(1) Activation Step

The activation step in the method for culturing lymphocytes according to one or more embodiments of the present invention is a step in which lymphocytes 30 and a culture liquid 40 are sealed in the culture container 10, and the culture container 10 is arranged such that the immobilized surface 11 becomes a bottom surface, thereby to activate the lymphocytes 30.

As mentioned above, the antibodies 20 are immobilized on the immobilized surface 11. As such antibodies 20, anti-CD3 antibodies can be preferably used.

The type of the lymphocytes 30 is not particularly restricted, and NK cells, B cells, T cells and mononuclear cells or the like can be objects to be cultured.

As the culture liquid 40, one commonly used for culturing the lymphocytes 30 can be used. For example, a culture liquid to which Interleukin-2 has been added can be preferably used.

In this activation step, the lymphocytes 30 in the culture container 10 are activated since the CD3 as the receptor molecule is irritated by the anti-CD3 antibodies that have been immobilized on the immobilized surface 11.

(2) Proliferation Step

The proliferation step in the method for culturing lymphocytes according to one or more embodiments of the present invention is a step in which the culture container 10 is inverted upside down to arrange the culture container 10 such that the non-immobilized surface 12 becomes a bottom surface, thereby to proliferate the lymphocytes 30.

By arranging the culture container 10 such that the non-immobilized surface 12 becomes a bottom surface, it becomes possible to culture the lymphocytes 30 on the side of the non-immobilized surface 12 in the culture container 10.

As a result, the lymphocytes 30 can be proliferated without being irritated by anti-CD3 antibodies that have been immobilized on the immobilized surface 11. Therefore, lowering in proliferation efficiency that occurs when the lymphocytes 30 are excessively irritated by the anti-CD3 antibodies can be prevented.

Method for Culturing Lymphocytes

Second Embodiment

Subsequently, a second embodiment of the method for culturing lymphocytes according to one or more embodiments of the present invention will be explained with reference to FIG. 5. The method for culturing lymphocytes according to one or more embodiments of the present invention has, as shown in FIG. 5, steps of activation step (1), first proliferation step (2), volume-enlarging step (3) and second proliferation step (4).

That is, the method for culturing lymphocytes according to one or more embodiments of the present invention has a volume-enlarging step in the midst of the proliferation step. As a result, proliferation efficiency of lymphocytes can be further improved as compared with that in the first embodiment. In one or more embodiments, the proliferation step will be explained by subdividing it into three steps of (2) to (4) mentioned above. Other points are the same as those in the first embodiment.

(1) Activation Step

In the activation step in the method for culturing lymphocytes according to one or more embodiments of the present invention, by partitioning the culture container 10 by means of a partitioning member 50, the culture container 10 is divided into a culture part 10-1 and an enlargeable part 10-2.

The culture part 10-1 is a chamber where lymphocytes 30 and the culture liquid 40 are sealed to activate the lymphocytes 30.

The enlargeable part 10-2 is a chamber where no lymphocytes 30 and the culture liquid 40 are sealed, and used as a space that enlarges the culture part 10-1 in accordance with proliferation of the lymphocytes 30.

The lymphocytes 30 and the culture liquid 40 cannot pass between the culture part 10-1 and the enlargeable part 10-2.

Here, in general, cells have properties that they hardly proliferate unless they have a prescribed level or more of cell density at the initial stage of culture. Therefore, it is preferred that the volume of the culture part 10-1 be adjusted such that it is small at the initial stage of culture and then is increased in size later.

Further, FIG. 5 shows a step in which the culture container 10 is partitioned by using a clip as a partitioning member 50 and then the clip is removed later to allow the whole of the culture container 10 to be the culture part 10-1. The manner of partitioning the culture container 10 is not limited thereto. For example, the culture part 10-1 may be continuously changed by using a roller as a partitioning member 50. It is also possible to change the culture part 10-1 multiple times into an arbitrary size.

Subsequently, the lymphocytes 30 and the culture liquid 40 are sealed in the culture part 10-1 in the culture container 10, and then, the culture container 10 is arranged such that the immobilized surface 11 in the culture part 10-1 becomes a bottom surface, whereby the lymphocytes 30 are activated.

During this activation step, the lymphocytes 30 in the culture part 10-1 are activated by the anti-CD3 antibodies that have been immobilized on the immobilized surface 11.

(2) First Proliferation Step

Subsequently, the culture container 10 is inverted upside down and the culture container 10 is arranged such that the non-immobilized surface 12 becomes a bottom surface, whereby the lymphocytes 30 are proliferated.

That is, by arranging the culture container 10 such that the non-immobilized surface 12 becomes a bottom surface, it becomes possible to culture the lymphocytes 30 on the non-immobilized surface side 12 in the culture part 10-1. As a result, the lymphocytes 30 can be proliferated without being irritated by the anti-CD3 antibodies that have been immobilized on the immobilized surface 11. Therefore, it becomes possible to proliferate lymphocytes efficiently in a single container.

(3) Volume-Enlarging Step

A volume-enlarging step is a step of enlarging the volume of the culture part 10-1 by moving or removing the partitioning member 50.

By this step, it becomes possible to adjust the volume of the culture part 10-1 in accordance with the number of the lymphocytes 30 that have been proliferated. As a result, the efficiency of proliferation of the lymphocytes 30 can further be improved.

(4) Second Proliferation Step

A second proliferation step is a step of continuously conducting culturing of the lymphocytes 30 in a state where the culture part 10-1 in the culture container 10 is enlarged. At this time, the culture container 10 is in the state where the non-immobilized surface 12 is arranged such that the non-immobilized surface 12 becomes a bottom surface.

As a result, the lymphocytes 30 can be proliferated without being irritated by the anti-CD3 antibodies that have been immobilized on the immobilized surface 11, and it becomes possible to prevent lowering in rate of proliferation of the lymphocytes 30 due to an excessive density of the lymphocytes 30 in the culture part 10-1.

In the meantime, by using plural clips or rollers as the partitioning member 50, the steps (3) and (4) are repeated plural times, whereby enlargement of the volume of the culture part 10-1 in a stepwise manner.

As explained hereinabove, according to the method for culturing lymphocytes according to one or more embodiments of the present invention, by using the culture container 10 according to one or more embodiments of the present invention, arranging the culture container 10 such that the immobilized surface 11 thereof becomes a bottom surface to activate the lymphocytes 30, and thereafter, arranging the culture container 10 such that the non-immobilized surface 12 thereof becomes a bottom surface to proliferate the lymphocytes 30.

Therefore, it is possible to prevent the lymphocytes 30 from being excessively irritated by the antibodies 20, whereby activation and proliferation of the lymphocytes 30 can be conducted efficiently in a single container.

Further, it is also possible to adjust the volume of the culture part 10-1 in the culture container 10 in accordance with the number of cells of proliferated lymphocytes 30, whereby the efficiency of proliferation of the lymphocytes 30 can be further improved.

Subsequently, a detailed explanation will be given on one or more embodiments of the method for producing a culture container and the immobilizing apparatus of the present invention.

[Method for Producing Culture Container]

The method for producing a culture container according to one or more embodiments of the present invention is a method for producing a culture container in which proteins are immobilized, characterized in that liquid droplets containing proteins being dissolved therein are injected and the liquid droplets are moved to part or the whole of an inner surface of the culture container.

Figure 9:
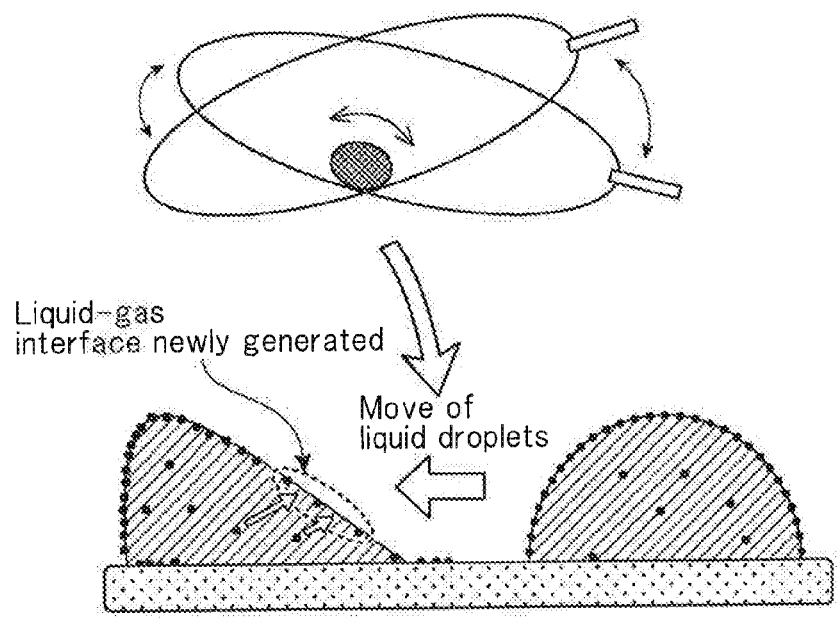
FIG. 9 is a view for explaining the principle of immobilizing in the method for producing a culture container according to one or more embodiments of the present invention.

First, a principle for enabling proteins to be immobilized efficiently on the inner surface of the culture container in the method for producing a culture container of one or more embodiments of the present invention will be explained with reference to FIG. 9.

When a solution containing proteins being dissolved therein is allowed to stand, the proteins exhibit their properties that they are adsorbed to the gas-liquid interface of this solution (BUNSEKI KAGAKU Vol. 59, No. 6. pp. 437-445 (2010)). Therefore, in the method for producing a culture container according to one or more embodiments of the present invention, liquid droplets containing proteins being dissolved therein are moved on the base member, whereby protein molecules concentrated in the gas-liquid interface are allowed to be in contact with the base member actively.

As mentioned above, by allowing liquid droplets to roll in the container to allow the gas-liquid interface to move in the container, proteins are adsorbed to the base member on the borderline of the gas, the liquid and the base member. When proteins are adsorbed to the base member, proteins in the liquid droplets are adsorbed to a newly generated gas-liquid interface. Then, if the liquid droplets are moved on the inner surface of the container, due to the contact of the gas-liquid interface having a high protein concentration and the inner surface of the container, proteins are adsorbed to the container inner surface at a high probability.

As a result, according to the method for producing a culture container of one or more embodiments of the present invention, it is possible to allow proteins to be immobilized efficiently on the inner surface of the container.

For example, when proteins are immobilized only on the bottom surface of the container, it becomes possible to prevent loss of proteins caused by adsorption of proteins to the upper surface of the container.

In one or more embodiments, the culture container means all of containers used in culturing cells, and includes containers used for activation and/or proliferation of cells.

No specific restrictions are imposed on the shape of the culture container in one or more embodiments of the present invention, and a bag-shaped culture bag made of a soft packaging material or a flask made of glass or polystyrene can be preferably used.

For example, a culture bag having opposing walls on the container inner surface can be preferably used, and proteins are immobilized on part or the whole of one or both of the inner surface of the culture bag, whereby the culture bag according to one or more embodiments of the present invention can be produced.

Figure 10A:
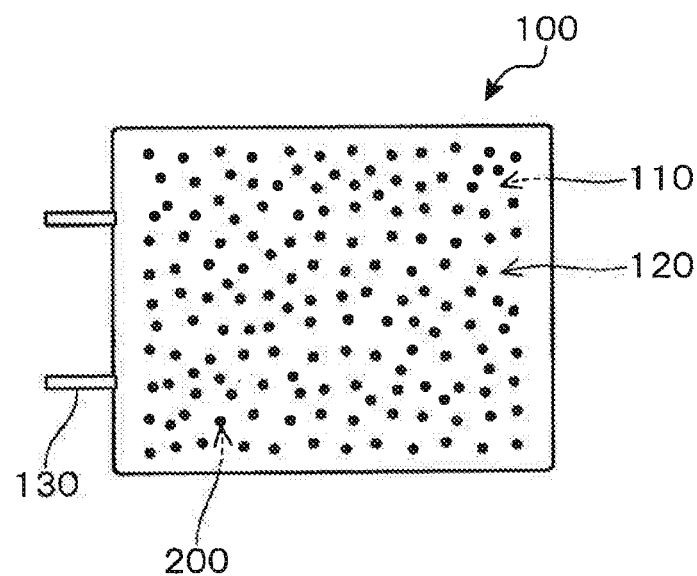
FIG. 10A is a view showing a culture bag in which antibodies are immobilized obtained by the method for producing a culture container according to one or more embodiments of the present invention.
Figure 10B:
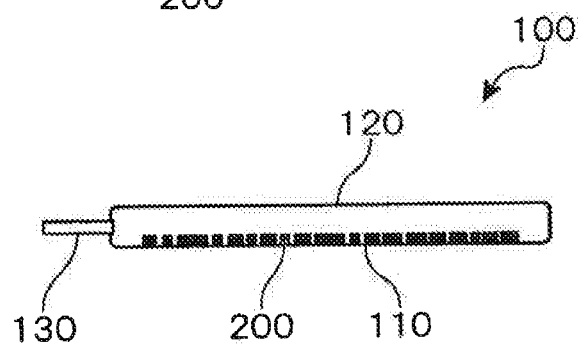
FIG. 10B is a view showing a culture bag in which antibodies are immobilized obtained by the method for producing a culture container according to one or more embodiments of the present invention.

Specifically, as shown in FIG. 10, one of the opposing inner surfaces of a culture bag 100 can be a immobilized surface 110 in which proteins 200 are immobilized (bottom surface of the container in FIG. 10), and the other one of the inner surfaces of the culture bag can be a non-immobilized surface 120 in which no proteins 200 are immobilized (upper surface of the container in FIG. 10).

The culture bag 100 is provided with the tube 130, and through this tube 130, the liquid droplets containing proteins dissolved therein and a gas can be introduced into or removed from the culture bag 100. In the example shown in this figure, the culture bag 100 is provided with two tubes 130. However, one or three or more tubes 130 may be provided.

It is preferred that the culture bag 100 be formed by using a film having permeability for a gas required for culturing cells. As the material for such culture bag 100, a polyolefin-based resin such as polyethylene and polypropylene can be preferably used.

In one or more embodiments of the present invention, the proteins 200 to be immobilized on the culture bag 100 are not particularly restricted. Antibodies such as anti-CD3 antibodies and cell adhesive proteins such as fibronectin, collagen and laminin can be used. Anti-CD3 antibodies are preferably used for activating lymphocytes. Cell adhesive proteins are preferably used in order to allow adhesive cells efficiently on the culture base member.

When anti-CD3 antibodies are immobilized as the proteins 200, it is preferred that the anti-CD3 antibodies be immobilized at a concentration of 10 to 300 $ng/cm^2$. If the anti-CD3 antibodies are immobilized at a concentration of 10 $ng/cm^2$ or more, it is possible to effectively activate lymphocytes, and thereafter, proliferate the lymphocytes efficiently. On the other hand, immobilizing at a concentration of 300 $ng/cm^2$ or higher is not preferable, since anti-CD3 antibodies float in a culture liquid in the culture bag 100 and excessively irritate lymphocytes.

The liquid droplets for dissolving proteins in one or more embodiments of the present invention are not particularly restricted. However, a phosphate buffer solution can be preferably used.

Further, it is preferred that the size of the liquid droplets (amount of liquid droplets) containing proteins dissolved therein be 1 cc to 20 cc. Since a friction force acts between the liquid droplets and the inner surface when the liquid droplets move on the inner surface of the culture bag 100, if the droplets are too small, they cannot move appropriately. Further, if the size of the liquid droplets is too large, the concentration of proteins in the liquid droplets is lowered, and the area of the gas-liquid interface per volume of the liquid droplet is reduced, whereby the adhesion efficiency is lowered. In this respect, the size of the liquid droplet is preferably 1 cc to 10 cc, further preferably 1 cc to 5 cc, and further more preferably around 2 cc.

In one or more embodiments of the present invention, although the gas to be sealed in the culture bag 100 is not particularly restricted, an inert gas is preferable. Air, nitrogen gas or the like can be used. Such a gas can be injected into the culture bag 100 through the tube 130 by a gas supply apparatus, for example.

The amount of a gas to be sealed in the culture bag 100 is preferably 0.1 to 4 ml, further preferably 1 to 3 ml, per $cm^2$ of the bottom surface of the culture bag 100. If the amount of the gas to be sealed is allowed to be in this range, it is possible to prevent the opposing walls on the inner surface of the culture bag 100 from contacting each other, whereby the liquid droplets containing the proteins 200 being dissolved therein can be efficiently moved in the culture bag 100.

The culture bag 100 can be produced as follows, for example.

First, low-density polyethylene is extruded by using a plastic extrusion molding apparatus to form a film. By using an impulse sealer, the culture bag 100 is produced from this film. As shown in FIG. 10, the culture bag 100 is produced with the tube 130 being attached thereto.

Subsequently, the culture bag 100 is mounted on a mounting table, and a prescribed amount of a gas is sealed. At that time, a buffer solution in which the proteins 200 are dissolved is continuously sealed. Then, by swinging or the like of the culture bag 100, the liquid droplets of the buffer solution are moved on the bottom surface of the culture bag 100. As a result, the proteins 200 contained in the buffer solution are adhered to the bottom surface of the culture bag 100, whereby the culture bag 100 in which the proteins 200 are immobilized can be obtained.

[Immobilizing Apparatus]

Figure 11:
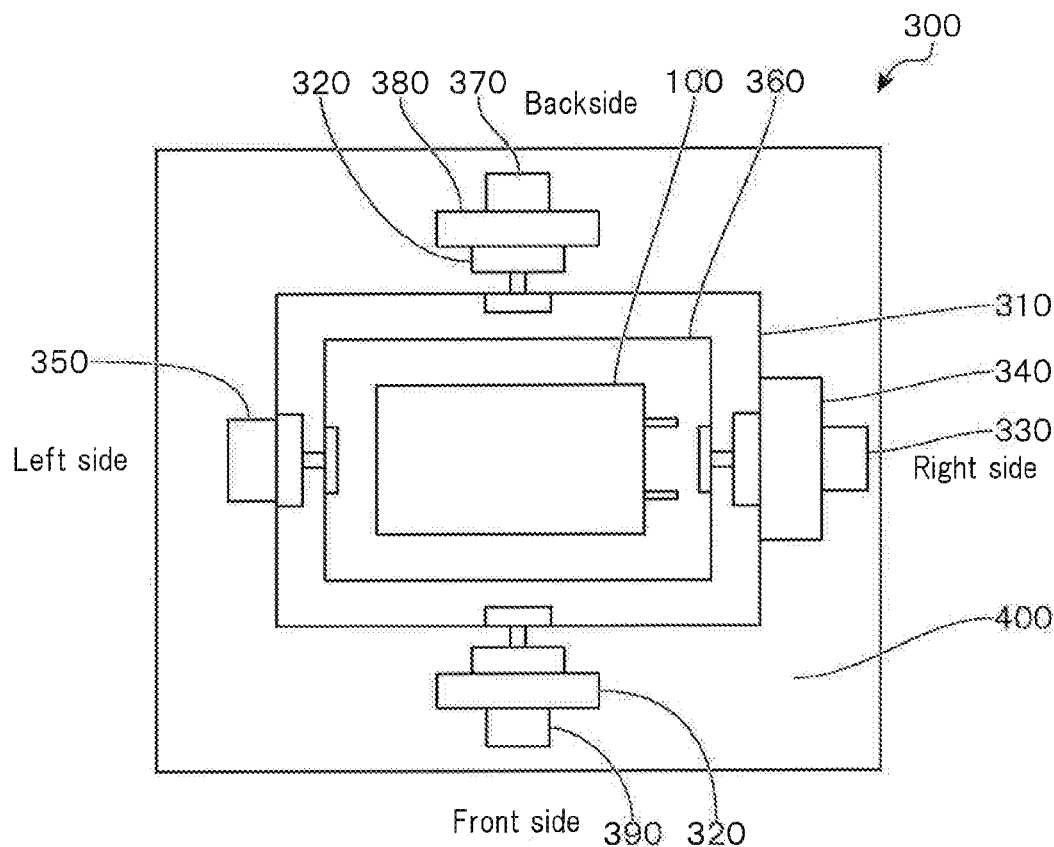
FIG. 11 is a view (plan view) showing a immobilizing apparatus according to one or more embodiments of the present invention.
Figure 12:
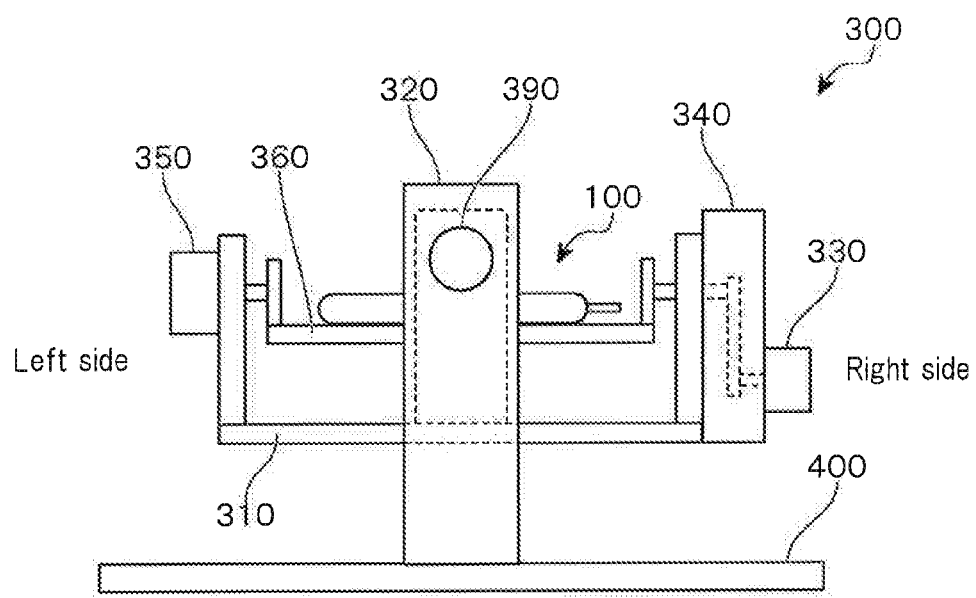
FIG. 12 is a view (front view) showing an immobilizing apparatus according to one or more embodiments of the present invention.
Figure 13:
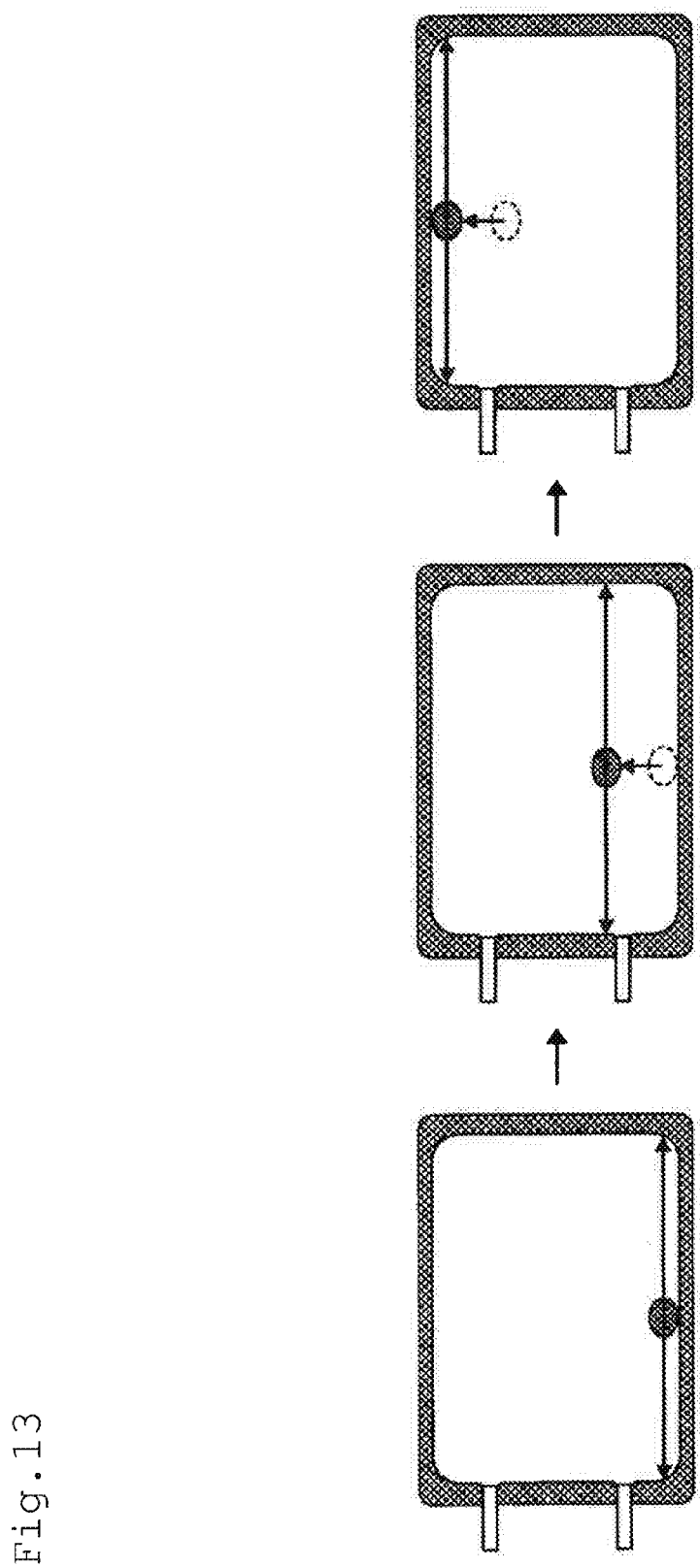
FIG. 13 is a view showing the manner of immobilizing by the immobilizing apparatus according to one or more embodiments of the present invention.
Figure 14A:
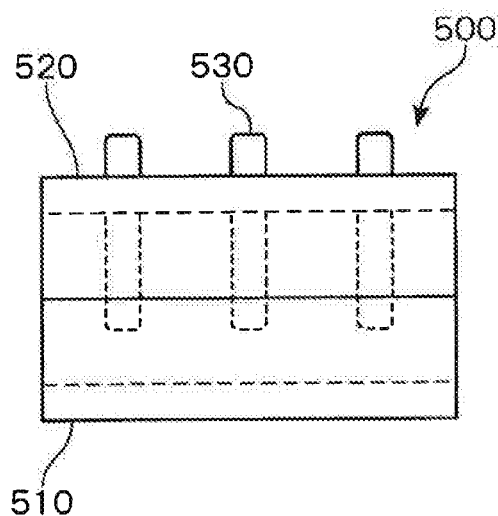
FIG. 14A is a front view showing retention means in the immobilizing apparatus according to one or more embodiments of the present invention.
Figure 14B:
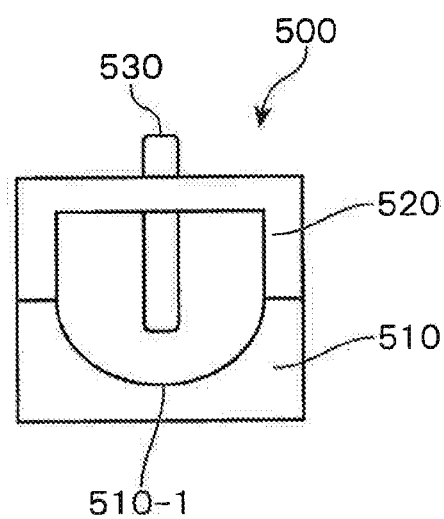
FIG. 14B is a side view showing retention means in the immobilizing apparatus according to one or more embodiments of the present invention.
Figure 15A:
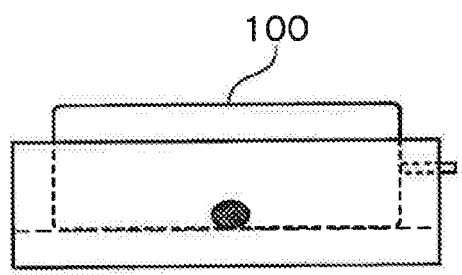
FIG. 15A is a view showing the state of usage of the retention means in the immobilizing apparatus according to one or more embodiments of the present invention.
Figure 15B:
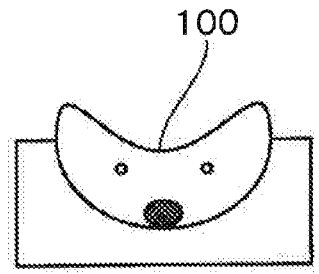
FIG. 15B is a view showing the state of usage of the retention means in the immobilizing apparatus according to one or more embodiments of the present invention.
Figure 15C:
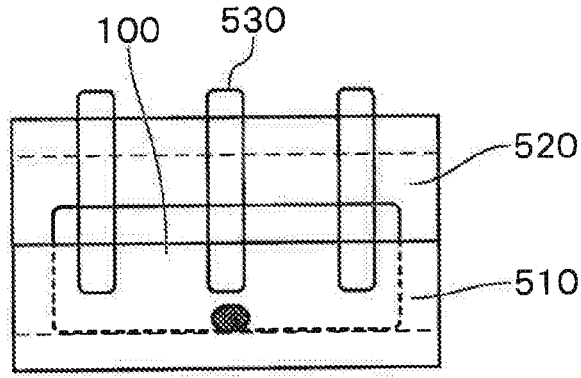
FIG. 15C is a view showing the state of usage of the retention means in the immobilizing apparatus according to one or more embodiments of the present invention.
Figure 15D:
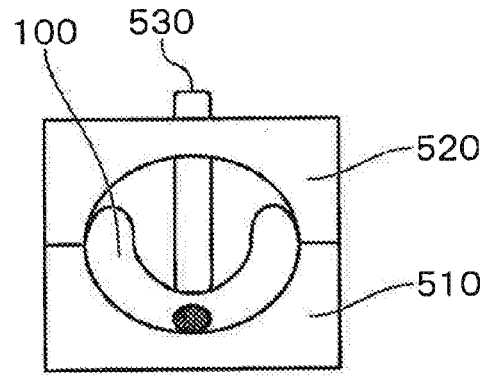
FIG. 15D is a view showing the state of usage of the retention means in the immobilizing apparatus according to one or more embodiments of the present invention.

Subsequently, an immobilizing apparatus of one or more embodiments of the present invention that can be preferably used in the method for producing a culture container of one or more embodiments of the present invention and a retention means used in this immobilizing apparatus will be explained with reference to FIGS. 11 to 15. FIG. 11 shows a plan view of the immobilizing apparatus and FIG. 12 is a front view of the immobilizing apparatus. FIG. 13 shows a manner of immobilizing by means of the immobilizing apparatus. FIG. 14 shows a front view and a lateral view of the retention means. FIG. 15 shows how the retention means is used.

In FIG. 11, the lower side shows the front side of the immobilizing apparatus 300, the upper side shows the back side of the immobilizing apparatus 300, the left side shows the left side of the immobilizing apparatus 300 and the right side shows the right side of the immobilizing apparatus 300, respectively. In this figure, the lateral direction (the longitudinal direction of the mounting table mentioned later) is taken as the X-axis direction and the vertical direction (the lateral direction of the mounting table) is taken as the Y-axis direction.

The immobilizing apparatus 300 is provided with a supporting table 310 for moving in the X-axis direction and a supporting table 360 for moving in the Y-axis direction. The culture bag 100 seals liquid droplets containing proteins being dissolved therein and a prescribed amount of a gas, and then is mounted on the supporting table 360 for moving in the Y-axis direction. The supporting table 310 for moving in the X-axis direction and the supporting table 360 for moving in the Y-axis direction are moved integrally. Hereinafter, the supporting table 310 for moving in the X-axis direction and the supporting table 360 for moving in the Y-axis direction may comprehensively be referred to as the "mounting table".

The supporting table 310 for moving in the X-axis direction is supported at the both sides (front and back sides) in the middle of the longitudinal direction by two vertically provided supporting columns 320 that are fixed to a base stand 400.

The supporting table 310 for moving in the X-axis direction is connected to a servo motor 330 for moving in the X-axis direction (driving means for moving in the longitudinal direction) through a gear box 340 for moving in the X-axis direction.

By driving this servo motor 330 for moving in the X-axis direction, the supporting table 310 for moving in the X-axis direction can move alternatively in the left-handed direction and the right-handed direction around the Y-axis direction. As a result, the supporting table 310 for moving in the X-axis direction can conduct seesaw movement laterally.

Accordingly, the liquid droplets in the culture bag 100 mounted on the supporting table containing proteins being dissolved therein can move laterally and reciprocally from the left end to the right end in the culture bag 100.

At this time, the angle of the rotational movement of the supporting table 310 for moving in the X-axis direction may be in a range of −10° to +10°, for example. In FIGS. 11 and 12, a case where the left side becomes high is minus (−) and a case where the right side becomes high is plus (+).

The speed of the rotational movement of the supporting table 310 for moving in the X-axis direction can be a speed at which the droplets containing proteins being dissolved therein move in the culture bag 100 at a speed of 5 m/min to 15 m/min, for example.

An origin limit detection sensor for the Y-axis 350 is used in order to detect the origin and the limit of the Y-axis.

The supporting table 360 for moving in the Y-axis direction is supported by the both sides (the left and right sides) in the middle of the lateral direction by two supporting parts that are vertically provided on the left and right end parts of the supporting table 310 for moving in the X-axis direction.

Further, the supporting table 360 for moving in the Y-axis direction is connected to a servo motor 370 (driving means for moving in the lateral direction) through a gear box 380 for moving in the Y-axis direction.

By driving this servo motor 370 for moving in the Y-axis direction, the supporting table 360 for moving in the Y-axis direction can conduct a rotational movement together with the supporting table 310 for moving in the X-direction with the X-axis direction being as a central axis alternatively in the left-handed direction and the right-handed direction. As a result, the mounting table can move laterally; i.e. conduct seesaw movement (move up and down in FIG. 11).

Therefore, the liquid droplets containing proteins being dissolved therein in the culture bag 100 mounted on the mounting table can move in the culture bag 100 from the lower end to the upper end.

At this time, the angle of the rotational movement of the supporting table 360 for moving in the Y-axis direction may be in a range of −50° to +50°, for example. In FIGS. 11 and 12, a case where the front side becomes high is minus (−) and a case where the back side becomes high is plus (+).

It is preferred that movement of liquid droplets in the Y-axis direction be conducted for a distance that is equal to or smaller than the size of the liquid droplets. By allowing the liquid droplets to move in the Y-axis direction and by allowing the liquid droplets to move in the X-axis direction from the left end to the right end in the culture bag 100, it is possible to allow the liquid droplets to move over the entire bottom surface of the culture bag 100, as well as to efficiently adsorb proteins contained in the liquid droplets in the culture bag 100.

An X-axis origin limit detection sensor 390 is used to detect the origin and limit of the X-axis.

Subsequently, an explanation will be made on the method for producing the culture bag 100 by using the immobilizing apparatus 300 of one or more embodiments of the present invention.

First, the culture bag 100 is mounted on the mounting table, and a prescribed amount of air is sealed. Then, liquid droplets containing proteins being dissolved therein are injected. Subsequently, by driving a servo motor 370 for moving in the Y-axis direction, as shown in FIG. 13, the mounting table is rotationally moved to the front side with the X-axis direction being the central axis. As a result, the liquid droplets are allowed to move to the end part at the front side of the culture bag 100.

Subsequently, by driving the servo motor 330 for moving in the X-axis direction, the mounting table is allowed to move rotationally in the lateral direction with the Y-axis direction being a central axis. As a result, the liquid droplets are allowed to move in the culture bag 100 laterally from the left end and the right end.

Subsequently, by driving the servo motor 370 for moving in the Y-axis direction, the mounting table is slightly moved rotationally to the backside, whereby the liquid droplets are slightly moved towards the backside. Then, by driving again the servo motor 330 for moving in the X-axis direction to allow the mounting table to move rotationally in a lateral direction, the liquid droplets in the culture bag 100 are allowed to move laterally from the left end to the right end. The above-mentioned operation was repeated until the liquid droplets are moved to the end part on the backside of the culture bag 100 and moved laterally from the left end to the right end.

As mentioned above, by allowing proteins to be adsorbed to the culture bag 100 by using the immobilizing apparatus 300, immobilizing efficiency of proteins can be further improved.

The immobilizing apparatus 300 of one or more embodiments of the present invention can be preferably used when proteins are immobilized not only to the culture bag 100 but also to a flask or other containers.

Next, an explanation will be made on a retention member used in the immobilizing apparatus of one or more embodiments of the present invention.

The retention member is a member for supporting the culture container such that the bottom surface thereof forms a semi-cylindrical shape, and is fixed on the mounting table or formed integrally with the mounting table.

As shown in FIG. 14, the retention member 500 is provided with a main body 510, an upper lid part 520 and a pressuring part 530.

The main body part 510 is provided with a semi-cylindrical recess part 510-1 for retaining the culture bag 100 in a curved state. The upper lid part 520 is attached to the main body part 510 by covering this recess part 510-1. The method for attaching the upper lid part 520 to the main body part 510 is not particularly restricted. For example, attaching by screwing can be given.

The upper lid part 520 is provided with a pressing part 530 for pressing the culture bag 100 from the outside. By allowing the pressing part 530 to move downwardly, the culture bag 100 arranged in the recess part 510-1 of the main body part 510 is pressed, whereby the bottom surface of the culture bag 100 can be stabilized in a semi-cylindrical shape.

The method for attaching the pressing part 530 to the upper lid part 520 is not particularly restricted as long as the pressing part 530 can be moved downwardly and the culture bag 100 can be pressed. For example, the upper lid part 520 and the pressing part 530 are engaged by a screw.

The shape of the pressing part 530 is not limited to a rod as shown in FIG. 14. The pressing part 530 may be in other shapes. For example, it is preferable to keep the bottom surface of the culture bag 100 in a semi-cylindrical shape by allowing the lower end of the pressing part 530 to be branched or by allowing the pressing part 530 to be semisphere more stably with the lower part thereof to be curved.

FIG. 14 shows a state in which three pressing parts 530 are attached to the upper lid part 520. The number of the pressing parts 530 to be attached is not particularly limited. It may be one, two or four or more.

FIG. 15 shows a state where the retention member 500 is used, and shows how the culture bag 100 is retained by the retention member 500.

At first, in the recess part 510-1 of the main body part 510 of the retention member 500, the culture bag 100 is arranged. At this time, the culture bag is arranged such that the bottom surface of the culture bag 100 becomes curved along the recess part 510-1.

Subsequently, the upper lid part 520 is attached to the main body part 510, and the pressing part 530 is moved downward. As a result, the bottom surface of the culture bag 100 can be kept in a semi-cylindrical shape.

The retention member 500 is fixed to the mounting table of the immobilizing apparatus 300 such that the direction of the central axis of the semi-cylindrical shape of the recess part 510-1 becomes identical with the longitudinal direction of the mounting table. Further, the retention member 500 can be formed integrally with the mounting table with this positional relationship.

If the culture bag 100 is retained by such retention member 500 such that the bottom surface of the culture bag 100 to be kept in a semi-cylindrical shape, and the liquid droplets in the culture bag 100 are moved in the Y-axis direction, since the liquid droplets are always positioned on the lowermost part of the recess part 510-1 of the retention member 500, the movement of the liquid droplets in the Y-axis direction can be precisely controlled.

As explained hereinabove, according to the method for producing a culture container of one or more embodiments of the present invention, it is possible to allow proteins to be immobilized efficiently on the inner surface of the culture container. As a result, the time required for immobilizing can be shortened, and at the same time, adsorption efficiency to the culture container can be improved, whereby a required amount of immobilizing can be conducted with a small amount of proteins. Accordingly, the amount of proteins discarded without being immobilized can be reduced. Further, by using the immobilizing apparatus of one or more embodiments of the present invention, it is possible to further improve the efficiency of immobilizing of proteins. In addition, by using the retention member, movement of liquid droplets can be controlled more precisely, whereby efficiency of immobilizing of proteins can be further improved.

EXAMPLES

Figure 7:
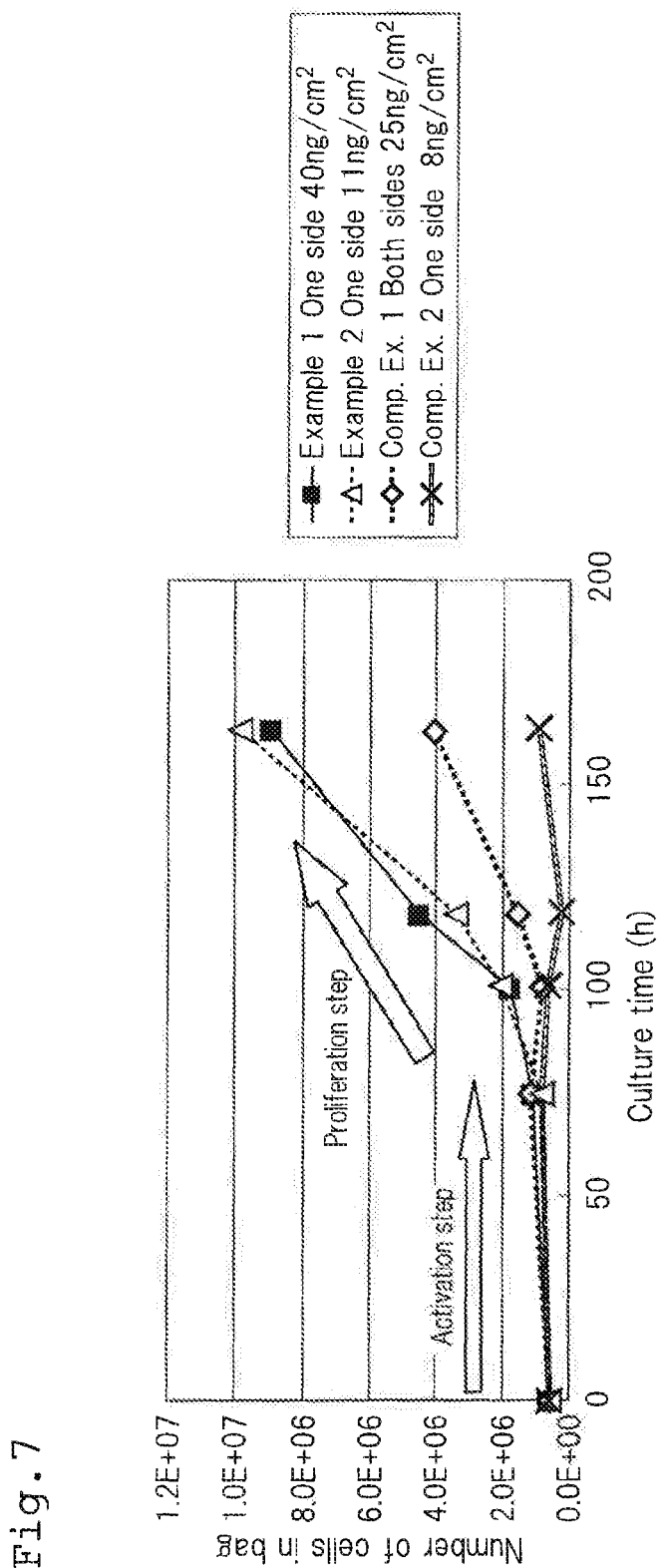
FIG. 7 is a graph showing the results of an experiment conducted on Examples and Comparative Examples of the culture container and the method for culturing lymphocytes according to one or more embodiments of the present invention.
Figure 8:
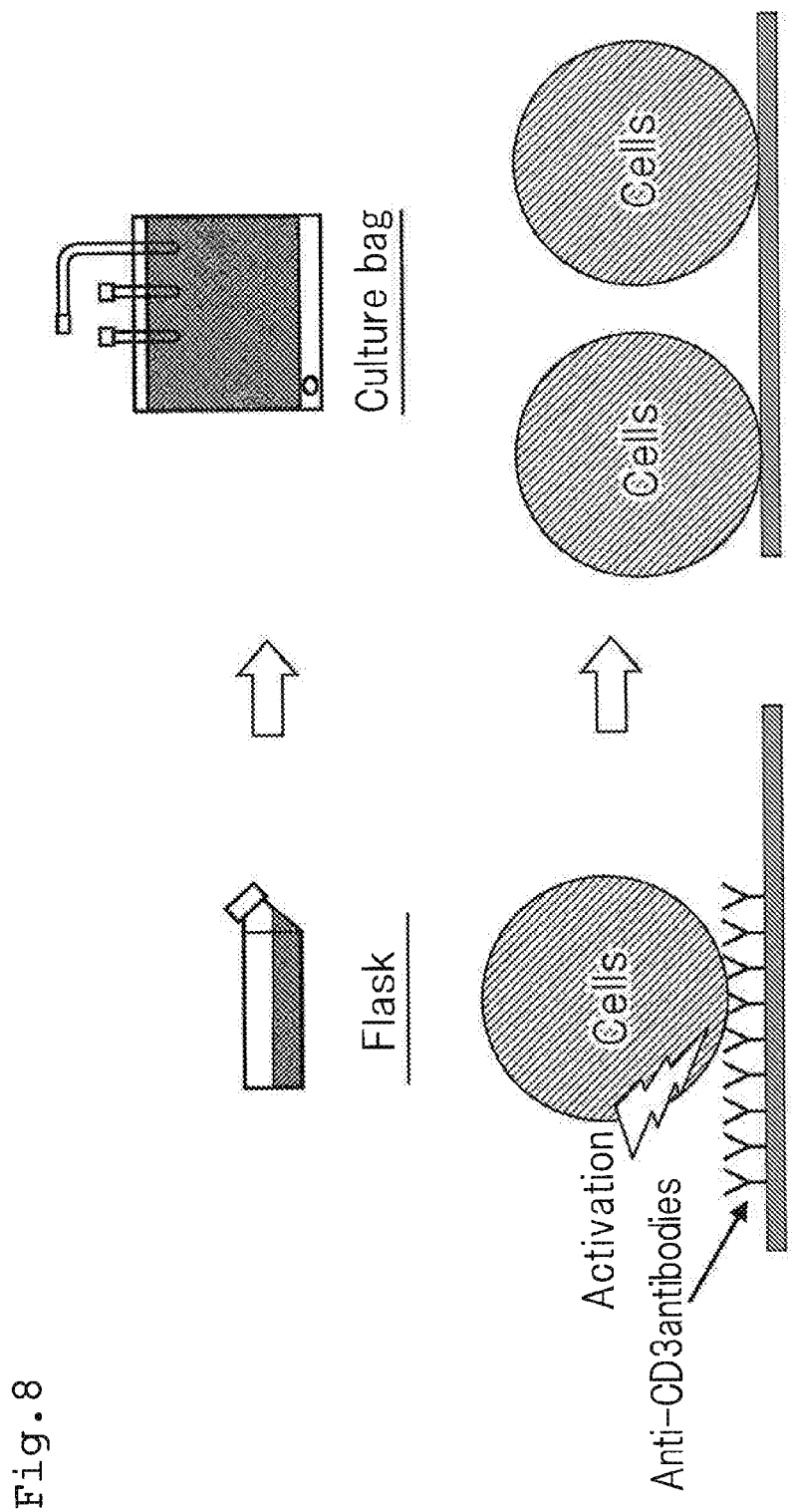
FIG. 8 is a view showing a conventional method for culturing lymphocytes.

Hereinbelow, the Examples and Comparative Examples of the culture container and the method for culturing lymphocytes will be explained with reference to FIGS. 6 and 7. FIG. 6 is a schematic view showing the Examples and the Comparative Examples, and FIG. 7 is a graph showing the results of experiments conducted in the Examples and the Comparative Examples. FIG. 6 shows a difference between the Examples and the Comparative Examples, and the enlargement of the volume of the culture part is omitted.

Experiment 1

Production of Culture Container

Example 1

By using Labo Plastmill (manufactured by Toyoseiki Seisakusho, Co., Ltd.) as a plastic extrusion molding apparatus, low-density polyethylene was extruded to form a 100 μm-thick film. Subsequently, by using an impulse sealer, a bag of 11 cm×22.5 cm (about 225 cm$^2$) was prepared from this film. This bag was sterilized with y rays to be used for an experiment.

Subsequently, about 600 ml of air was sealed in this bag, followed by sealing of 10 ml of a phosphate buffer solution (manufactured by Lifetechnologies, Japan) containing 50 μg of anti-CD3 antibodies (manufactured by Miltenyi Biotec K.K.) being dissolved therein. At this time, sealing was conducted such that the liquid droplets of the phosphate buffer solution were brought into contact with only one surface (immobilizing surface) of the inner surfaces of the bag.

Then, the bag was swung by hands for 1 minute at 26° C., thereby to move the liquid droplets of the phosphate buffer solution on the bottom surface in the bag at a speed of 10 m/min, whereby a immobilized surface was formed in the bag to produce a culture container.

In the meantime, the culture containers were produced in a quantity of two. One of the culture containers was used for measuring the concentration of antibodies that were immobilized and the other was used for a test for culturing lymphocytes. The same is applied to other Examples and Comparative Examples.

Measurement of the concentration of antibodies that were immobilized was conducted as follows.

First, the liquid in the culture container was removed, and 500 μl of a phosphate buffer solution (same as above) comprising 1% sodium dodecyl sulfate (manufactured by Sigma-Aldrich Japan) was brought into contact with the immobilized surface, and the container was allowed to stand for 30 minutes. Then, strong vibration was applied by means of a PresentMixer (manufactured by TAITEC Co., Ltd.), whereby adsorbed antibodies were peeled off. The amount of the antibodies in the peeling liquid was measured by means of Micro BCA™ Protein Assay Kit (manufactured by ThermoFisher Scientific K.K.), and adsorption concentration was calculated by dividing with an immobilizing area.

As for the culture container in Example 1, anti-CD3 antibodies were immobilized on only one of the inner surfaces thereof.

As a result of measurement of the concentration of antibodies that were immobilized in the culture container in Example 1, the concentration of the anti-CD3 antibodies in the immobilized surface was 40 ng/cm$^2$.

Example 2

A bag of 11 cm×22.5 cm (about 225 cm$^2$) was prepared in the same manner as in Example 1.

Subsequently, about 600 ml of air was sealed in this bag, followed by sealing of 10 ml of a phosphate buffer solution (manufactured by Lifetechnologies, Japan) containing 5 μg of anti-CD3 antibodies (manufactured by Miltenyi Biotec K.K.) being dissolved therein. As for other points, the same procedures as those in Example 1 were conducted to produce the culture container in Example 2.

In the culture container in Example 2, anti-CD3 antibodies were immobilized on only one of the inner surfaces thereof.

As the result of measurement of the concentration of the immobilized antibodies in the culture container in Example 2, the concentration of the anti-CD3 antibodies in the immobilized surface was 11 ng/cm$^2$.

Comparative Example 1

A bag of 11 cm×22.5 cm (about 225 cm$^2$) was prepared in the same manner as in Example 1.

Subsequently, in this bag, 10 ml of a phosphate buffer solution (manufactured by Lifetechnologies, Japan) containing 50 μg of anti-CD3 antibodies (manufactured by Miltenyi Biotec K.K.) being dissolved therein was sealed. The liquid droplets of the phosphate buffer solution were brought into contact with the upper and lower surfaces of the bag, and the bag was allowed to stand at 26° C. for 60 minutes. Then, the inside of the bag was washed with 40 ml of the phosphate buffer solution three times, whereby the culture container of Comparative Example 1 was produced.

In the culture container in Comparative Example 1, anti-CD3 antibodies were immobilized on the both inner surfaces thereof.

As a result of measurement of the concentration of the immobilized antibodies in the culture container in Comparative Example 1, the concentration of the anti-CD3 antibodies in the immobilized surface was 25 ng/cm$^2$.

Comparative Example 2

A bag of 11 cm×22.5 cm (about 225 cm$^2$) was prepared in the same manner as in Example 1.

Subsequently, about 600 ml of air was sealed in this bag, followed by sealing of 10 ml of a phosphate buffer solution (manufactured by Lifetechnologies, Japan) containing 5 μg of anti-CD3 antibodies (manufactured by Miltenyi Biotec K.K.) being dissolved therein. At this time, sealing was conducted such that the liquid droplets of the phosphate buffer solution were brought into contact with only one surface (immobilized surface) of the inner surface of the bag.

Then, the bag was swung by hands for 1 minute at 26° C. to move the liquid droplets of the phosphate buffer solution on the bottom surface in the bag at a speed of 10 m/min, whereby a immobilized surface was formed in the bag. Further, the inside of the bag was washed three times with 10 ml of the phosphate buffer solution, thereby to produce the culture container of Comparative Example 2.

In the culture container in Comparative Example 2, anti-CD3 antibodies were immobilized on only one inner surface thereof.

As a result of measurement of the concentration of the immobilized antibodies in the culture container in Comparative Example 2, the concentration of the anti-CD3 antibodies in the immobilized surface was 8 ng/cm².

Experiment 2

Culture of Lymphocytes (Activation Step)

Each of the culture containers obtained in Examples 1 and 2 and Comparative Examples 1 and 2 of Experiment 1 were partitioned by means of a clip such that the culture part became 5 cm×11 cm.

Subsequently, $5.8 \times 10^4$ human mononuclear cells (manufactured by Cell Applications, Inc.) were suspended in an ALyS505N-7 culture medium containing 10% fetal bovine serum (manufactured by Cell Science & Technology, Inc.) and 4 ml of the suspension was sealed in the culture container. The culture container was allowed to stand at 37° C. for 75 hours, thereby to activate lymphocytes.

In Examples 1 and 2 and Comparative Example 2, activation was conducted with the immobilized surface of the culture container facing downward. As for the culture container in Comparative Example 1, as mentioned above, the same amount of the anti-CD3 antibodies were immobilized on the both upper and lower surfaces of the inside thereof. Therefore, there is no distinction between the upper surface and the lower surface; that is, there is no distinction between the immobilized surface and the non-immobilized surface.

(Proliferation Step)

To the culture container that had completed the activation step, 4 ml of the above-mentioned culture medium was added. The culture container was inverted upside down, and in that state, the culture container was allowed to stand at 37° C. for 26 hours, thereby to proliferate the lymphocytes (first proliferation step in the second embodiment).

Subsequently, the clip was removed to enlarge the volume of the culture part of the culture container (volume enlargement step in the second embodiment). Then, 20 ml of the above-mentioned culture medium was added, and the container was allowed to stand at 37° C. for 62 hours to continue the proliferation of the lymphocytes (second proliferation step in the second embodiment).

At the timing of each operation after the start of the culture (after 75 hours, 75+26 (=101) hours, 75+26+62 (=163) hours, and 18 hours after the removal of the clip (75+26+18 (=119)), the number of the lymphocytes was counted. The results are shown in FIG. 7.

As shown in FIG. 7, in Examples 1 and 2 where 40 ng/cm² and 11 ng/cm² of anti-CD3 antibodies were immobilized only on one surface of the culture container, it became possible to significantly proliferate lymphocytes during the proliferation step. At this time, no significant difference in proliferation efficiency was observed between the immobilizing concentration of 40 ng/cm² (Example 1) and 11 ng/cm² (Example 2).

In Comparative Example 1 in which anti-CD3 antibodies were immobilized to the both surfaces of the culture container, it could be understood that the proliferation efficiency of lymphocytes in proliferation step was significantly lowered as compared with Examples 1 and 2.

Further, in Comparative Example 2 in which the concentration of the anti-CD3 antibodies to be immobilized was slightly reduced than that in Example 2, most of lymphocytes could not be proliferated during the proliferation step. From this result, it can be understood that it is preferable to allow the concentration of the anti-CD3 antibodies to be immobilized on the immobilizing surface to be about 10 ng/cm² or more.

Figure 18A:
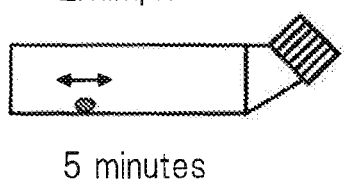
FIG. 18A is a schematic view showing Example 5 of the method for producing a culture container (culture flask in which antibodies are immobilized) according to one or more embodiments of the present invention.
Figure 18B:
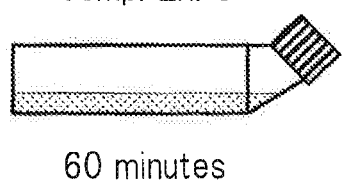
FIG. 18B is a schematic view showing Comparative Example 5 of the method for producing a culture container (culture flask in which antibodies are immobilized) according to one or more embodiments of the present invention.
Figure 18C:
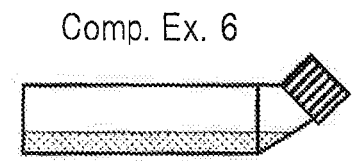
FIG. 18C is a schematic view showing Comparative Example 6 of the method for producing a culture container (culture flask in which antibodies are immobilized) according to one or more embodiments of the present invention.
Figure 19:
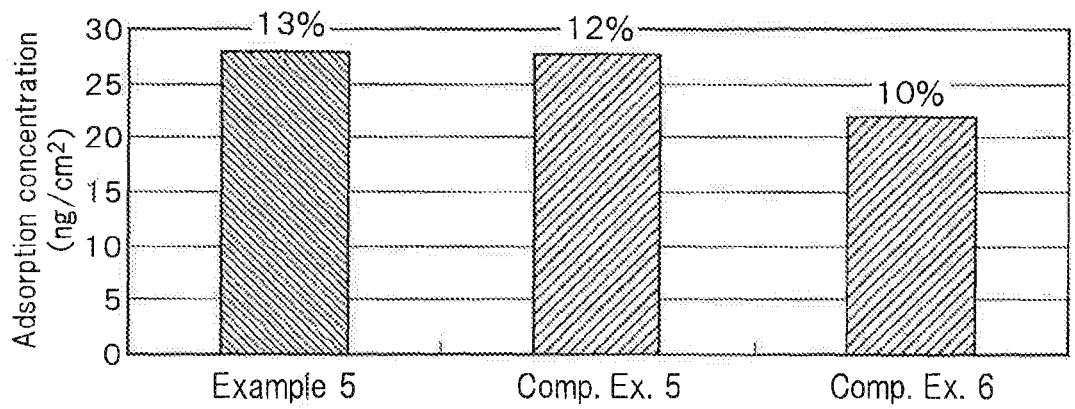
FIG. 19 is a graph showing the results of an experiment conducted in the Examples and the Comparative Examples of the method for producing a culture container (culture flask in which antibodies are immobilized) according to one or more embodiments of the present invention.
Figure 20A:
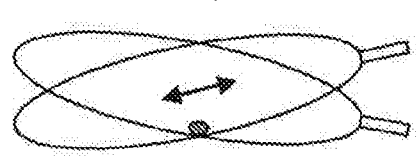
FIG. 20A is a schematic view showing Example 6 of the method for producing a culture container (culture bag in which fibronectin is immobilized) according to one or more embodiments of the present invention.
Figure 20B:
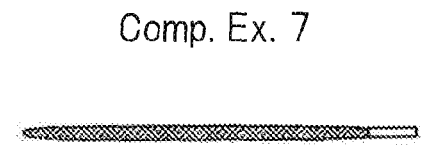
FIG. 20B is a schematic view showing Comparative Example 7 of the method for producing a culture container (culture bag in which fibronectin is immobilized) according to one or more embodiments of the present invention.
Figure 21:
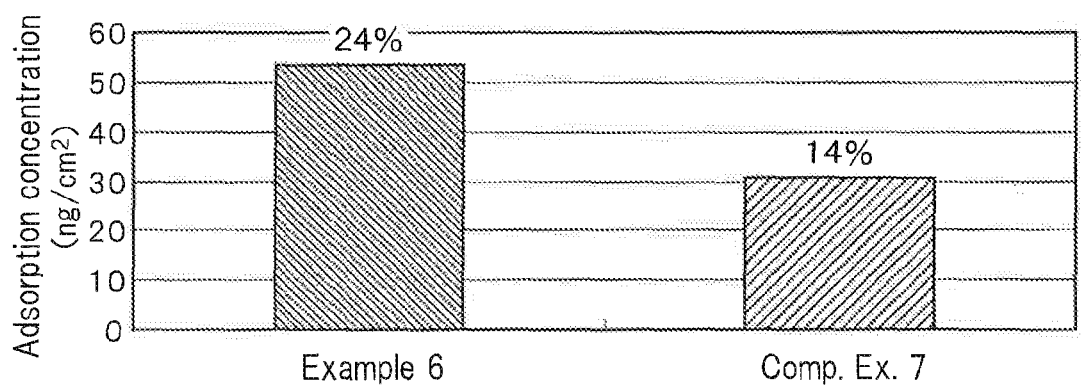
FIG. 21 is a graph showing the results of an experiment in the Examples and the Comparative Examples of the method for producing a culture container (culture bag in which fibronectin is immobilized) according to one or more embodiments of the present invention.

Subsequently, the Examples and the Comparative Examples of the method for producing a culture container according to one or more embodiments of the present invention will be explained with reference to FIGS. 16 to 21. FIGS. 16, 18 and 20 are schematic views showing the Examples and the Comparative Examples, and FIGS. 17, 19 and 21 are graphs showing the results of the experiments in the Examples and the Comparative Examples.

Experiment 3

Production of Culture Bag in which Antibodies are Immobilized

Example 3

By using a Labo Plastmill (manufactured by Toyo Seiki Kogyo Co., Ltd.) as a plastic extrusion molding apparatus, low-density polyethylene was extruded to form a 100 μm-thick film. Subsequently, by using an impulse sealer, a bag of 11 cm×22.5 cm (about 225 cm²) was prepared from this film. This bag was sterilized with γ rays to be used for an experiment.

Subsequently, this bag was mounted on the supporting table, and about 600 ml of air was sealed in this bag, followed by sealing of 10 ml of a phosphate buffer solution (manufactured by Lifetechnologies, Japan) containing 50 μg of anti-CD3 antibodies (manufactured by Miltenyi Biotec K.K.) being dissolved therein. At this time, sealing was conducted such that the liquid droplets of the phosphate buffer solution were brought into contact with only the bottom surface of the inner surface of the bag.

Then, the bag was swung by hands for 1 minute at 26° C., thereby to move the liquid droplets of the phosphate buffer solution on the bottom surface in the bag at a speed of 10 m/min. As a result, antibodies were adsorbed to the bottom surface in the bag, whereby a culture bag in which the antibodies were immobilized was produced.

The measurement of the antibodies that were immobilized was conducted as follows:

First, the liquid in the culture container was removed, and 500 μl of a phosphate buffer (same as above) comprising 1% sodium dodecyl phosphate (manufactured by Sigma-Aldrich Japan) was brought into contact with the immobilized surface, and the container was allowed to stand for 30 minutes. Then, strong vibration was applied by means of a Present-Mixer (manufactured by TAITEC Co., Ltd.), whereby adsorbed antibodies were peeled off. The amount of the antibodies in the peeling liquid was measured by means of Micro BCA™ Protein Assay Kit (manufactured by ThermoFisher Scientific K.K.). The amount of proteins adsorbed per unit area (hereinafter referred to as the adsorption concentration) was calculated by dividing the amount of antibodies by the area where the antibodies were immobilized.

In the culture container of Example 3, anti-CD3 antibodies were immobilized only on one surface (bottom surface) of the inside thereof. As a result of measuring the concentration of antibodies that had been immobilized in the culture container in Example 3, the concentration of the anti-CD3 antibodies adsorbed was found to be 41.5 ng/cm².

Example 4

A bag of 11 cm×22.5 cm (about 225 cm$^2$) was prepared in the same manner as in Example 3.

Subsequently, about 600 ml of air was sealed in this bag, followed by sealing of 10 ml of a phosphate buffer solution (manufactured by Lifetechnologies, Japan) containing 50 μg of anti-CD3 antibodies (manufactured by Miltenyi Biotec K.K.) being dissolved therein.

Then, the bag was swung by hands for 2.5 minutes at 26° C., thereby to move the liquid droplets of the phosphate buffer solution on the bottom surface in the bag at a speed of 10 m/min, thereby to allow antibodies to be adsorbed to the bottom surface in the bag. Subsequently, the bag was turned upside down, and then again swung by hand for 2.5 minutes, thereby to allow the liquid droplets to move on the bottom surface in the bag (upper surface before turning upside down) at a speed of 10 m/min. As a result, the antibodies were adsorbed on the both surfaces of the inner wall of the bag, whereby a culture bag in which the antibodies were immobilized was produced.

In the culture container of Example 4, the anti-CD3 bodies were immobilized on the both surfaces of the inside thereof. As a result of measuring the concentration of the antibodies that were immobilized in the culture container of Example 4, the concentration of anti-CD3 antibodies that were adsorbed was 31.2 ng/cm$^2$.

Comparative Example 3

A bag of 11 cm×22.5 cm (about 225 cm$^2$) was prepared in the same manner as in Example 3.

Subsequently, without sealing air in this bag, 10 ml of a phosphate buffer solution (manufactured by Lifetechnologies, Japan) containing 50 μg of anti-CD3 antibodies (manufactured by Miltenyi Biotec K.K.) being dissolved therein was sealed, and this phosphate buffer solution was allowed to be in contact with both the upper and lower surfaces of the bag, and the bag was allowed to stand at 26° C. for 60 minutes. The inside of the bag was washed three times with 40 ml of the phosphate buffer solution, whereby a culture bag in which the antibodies were immobilized was produced.

In the culture container of Comparative Example 3, the anti-CD3 antibodies were immobilized on the both surfaces of the inside thereof. As a result of measuring the concentration of the antibodies that were immobilized in the culture container in Comparative Example 3, it was found that the concentration of the anti-CD3 antibodies that were adsorbed was 26.1 ng/cm$^2$.

Comparative Example 4

A bag of 11 cm×22.5 cm (about 225 cm$^2$) was prepared in the same manner as in Example 3.

Subsequently, without sealing air in this bag, 10 ml of a phosphate buffer solution (manufactured by Lifetechnologies, Japan) containing 50 μg of anti-CD3 antibodies (manufactured by Miltenyi Biotec K.K.) being dissolved therein was sealed. Then, the bag was swung by hands at 26° C. for 5 minutes, whereby the liquid droplets of the phosphate buffer solution were allowed to move in the bag at a speed of 10 m/min. As a result, the antibodies were adsorbed to the inner surface of the bag. Further, the inside of the bag was washed three times with 10 ml of the phosphate buffer solution, whereby a bag in which the antibodies were immobilized was produced.

In the culture container of Comparative Example 4, the anti-CD3 antibodies were immobilized on the both surfaces of the inside thereof. As a result of measuring the concentration of the antibodies that were immobilized in the culture container in Comparative Example 4, it was found that the concentration of the anti-CD3 antibodies that were adsorbed was 23.8 ng/cm$^2$.

As shown in FIG. 17, efficiencies of adsorption (adsorption concentration×225 cm$^2$/50000 ng×100) of the antibodies on the culture container bottom surface per area of the antibodies in Example 3, Example 4, Comparative Example 3 and Comparative Example 4 were 19%, 14%, 12% and 11%, respectively.

That is, according to the method in Example 3, although the immobilizing time was 1 minute, the efficiency of adsorption was increased by about 60% as compared with the results of Comparative Example 3 in which the immobilizing was conducted for 60 minutes.

On the other hand, in Comparative Example 4 in which the antibodies were immobilized by moving the liquid droplets without sealing a gas in the culture container, the adsorption efficiency was small as compared with Comparative Example 3.

The reason for the fact that the adsorption efficiency in Example 4 was smaller than that in Example 3 is thought that the absorption area in Example 4 was twice as large as the absorption area of Example 3.

Further, when the results of Example 4 are compared with the results of Comparative Example 4, it can be understood that the adsorption efficiency could be improved by about 30% by allowing antibodies to be immobilized after incorporating a gas in the culture container while moving liquid droplets.

As mentioned above, according to the method for producing a culture container of one or more embodiments of the present invention, it is possible to allow a larger amount of antibodies to be immobilized in the culture container for a shorter period of time. In addition, it is possible to allow a larger amount of antibodies to be immobilized on a culture container by using antibodies in an amount smaller than that used in the conventional method.

Experiment 4

Production of Flask in which Antibodies are Immobilized

Example 5

In a suspension culture flask 800 (manufactured by Sumitomo Bakelite Co., Ltd., made of polystyrene having a bottom surface area of 225 cm$^2$), 10 ml of a phosphate buffer solution (manufactured by Lifetechnologies, Japan) containing 50 μg of anti-CD3 antibodies (manufactured by Miltenyi Biotec K.K.) being dissolved therein was sealed in the state of liquid droplets. The flask was swung by hands at 26° C. for 5 minutes, the liquid droplets of the phosphate buffer solution were allowed to move on the bottom surface in the bag at a speed of 10 m/min, and were adsorbed on the bottom surface of the flask, whereby a flask in which antibodies were immobilized was produced. The concentration of the anti-CD3 antibodies in the flask in which the antibodies were immobilized in Example 5 was 27.9 ng/cm$^2$.

Comparative Example 5

In a suspension culture flask 800 (manufactured by Sumitomo Bakelite Co., Ltd., made of polystyrene having a bottom surface area of 225 cm$^2$), 10 ml of a phosphate buffer solution (manufactured by Lifetechnologies, Japan) containing 50 µg of anti-CD3 antibodies (manufactured by Miltenyi Biotec K.K.) being dissolved therein was put, and the solution of the antibodies was spread over the entire surface. The flask was allowed to stand at 26° C. for 60 hours. As a result, the antibodies were adsorbed on the bottom surface of the flask, whereby a flask in which the antibodies were immobilized was produced. The concentration of the anti-CD3 antibodies in the flask in which the antibodies were immobilized in Comparative Example 5 was 27.6 ng/cm$^2$.

Comparative Example 6

In a suspension culture flask 800 (manufactured by Sumitomo Bakelite Co., Ltd., made of polystyrene having a bottom surface area of 225 cm$^2$), 10 ml of a phosphate buffer solution containing (manufactured by Lifetechnologies, Japan) 50 µg of anti-CD3 antibodies (manufactured by Miltenyi Biotec K.K.) being dissolved therein was put, and the solution of the antibodies was spread over the entire surface. The flask was allowed to stand at 26° C. for 5 minutes. As a result, the antibodies were adsorbed on the bottom surface of the flask, whereby a flask in which the antibodies were immobilized was produced. In the flask of Comparative Example 6 in which the anti-CD3 antibodies were immobilized, the concentration of the antibodies was 21.8 ng/cm$^2$.

As shown in FIG. 19, efficiencies of adsorption of the antibodies per area of the flask in Example 5, Comparative Example 5 and Comparative Example 6 was 13%, 12% and 10%, respectively.

Namely, as shown in Comparative Example 5, in the conventional method for immobilizing antibodies in which the antibodies are allowed to stand, the efficiency of absorption was 12% after the lapse of 60 minutes from the start of immobilizing. On the other hand, as shown in Example 5, in the method for producing a culture container according to one or more embodiments of the present invention, the efficiency of absorption could be 13% after the lapse of 5 minutes from the start of immobilizing.

Accordingly, it has been revealed that, according to the method for producing a culture container of one or more embodiments of the present invention, even if proteins are immobilized in a flask, an equivalent amount of proteins can be immobilized for a shorter period of time as compared with the conventional methods.

Experiment 5

Production of Culture Bag in which Fibronectin is Immobilized

Example 6

A bag of 11 cm×22.5 cm (about 225 cm$^2$) was prepared in the same manner as in Example 3.

Subsequently, about 600 ml of air was sealed in this bag, and then 10 ml of a phosphate buffer solution (manufactured by Lifetechnologies, Japan) containing 50 µg of human plasma fibronectin (manufactured by Sigma-Aldrich Japan) being dissolved therein was continuously sealed in the liquid droplet state.

The bag was swung by hands for 1 minute at 26° C., whereby the liquid droplets of the phosphate buffer solution were allowed to move on the bottom surface in the bag at a speed of 10 m/min. As a result, the fibronectin was adsorbed to the bottom surface of the bag, whereby a bag in which fibronectin was immobilized was produced.

In the culture container of Example 6, fibronectin was immobilized only on one side (bottom surface) in the inside thereof. As a result of measuring the concentration of immobilized fibronectin for the culture container of Example 6, it was found that the concentration of fibronectin adsorbed was 53.6 ng/cm$^2$.

Comparative Example 7

A bag of 11 cm×22.5 cm (about 225 cm$^2$) was prepared in the same manner as in Example 3.

Subsequently, without sealing air in this bag, 10 ml of a phosphate buffer solution (manufactured by Lifetechnologies, Japan) containing 50 µg of human plasma fibronectin (manufactured by Sigma-Aldrich Japan) being dissolved therein was sealed. The droplets of the phosphate buffer solution were brought into contact with the both upper and lower surfaces in the bag, and the bag was allowed to stand at 26° C. for 60 minutes. The inside of the bag was washed three times with 40 ml of the phosphate buffer solution, whereby a culture bag in which fibronectin was immobilized was produced.

In the culture container of Comparative Example 7, fibronectin was immobilized on both surfaces in the inside thereof. As a result of measuring the concentration of immobilized fibronectin for the culture container of Comparative Example 7, it was found that the concentration of fibronectin adsorbed was 30.7 ng/cm$^2$.

As shown in FIG. 21, efficiencies of adsorption of the fibronectin per area of the culture container in Example 6 and Comparative Example 7 were 24% and 14%, respectively.

Namely, when fibronectin is used as protein, according to the method for producing a culture container of one or more embodiments of the present invention, it is possible to allow fibronectin to be immobilized in an absorption efficiency that is higher by 70% than that of the conventional methods.

Therefore, according to the method for producing a culture container of one or more embodiments of the present invention, it has been revealed that proteins other than antibodies can be immobilized efficiently for a short period of time.

Experiment 6

Production of a Culture Bag in which Antibodies are Immobilized by Using an Immobilizing Apparatus Example 7

A bag of 8 cm×20 cm (about 160 cm$^2$) was prepared in the same manner as in Example 3.

Subsequently, this bag was mounted on the retention member in the immobilizing apparatus. By using the pressing part, the bag was fixed such that the bottom surface thereof became semi-cylindrical. Subsequently, about 280 ml of air was sealed, and 2 ml of a phosphate buffer solution (manufactured by Lifetechnologies, Japan) containing 10 µg of anti-CD3 antibodies (manufactured by Miltenyi Biotec K.K.) being dissolved therein was continuously sealed in the state of liquid droplets.

As shown in FIG. 13, the mounting table in the immobilizing apparatus was inclined by about −50° in the Y-axis direction (rotational movement with the X-axis direction being a central axis) to allow the liquid droplets to move towards the end part of the culture bag. Subsequently, the mounting table was rotated in the X-axis direction by −10° to 10° (rotational movement with the Y-axis direction being a central axis) to allow the liquid droplets to move towards the X-axis direction, whereby the liquid droplets were moved laterally in the culture bag reciprocally from the left end to the right end.

Subsequently, the mounting table was rotated by 10° in the Y-axis direction to allow the liquid droplets to move slightly towards the backside. Subsequently, the mounting table was again rotated in the X-axis direction by −10° to 10° to allow the liquid droplets to move in the X-axis direction, whereby the liquid droplets were laterally moved in the culture bag reciprocally from the left end to the right end.

The operations mentioned above were repeated until the rotation angle in the Y-axis direction (X-axis rotation angle) became 50°, whereby the liquid droplets were moved over the entire bottom surface of the culture bag. Taking this operation as one cycle, four cycles were conducted (immobilizing time: 3.5 minutes, temperature: 26° C.), and the amount of the antibodies that were immobilized was measured.

In the culture container of Example 7, the anti-CD3 antibodies were immobilized on only one surface in the inside thereof. As a result of measuring the concentration of immobilized antibodies for the culture container in Example 7, it was found that the concentration of the anti-CD3 antibodies adsorbed was 30.1 ng/cm$^2$.

Accordingly, the efficiency of adsorption of the antibodies per area of the culture container in Example 7 (adsorption concentration×160 cm$^2$/10000 ng×100) was 48%. This adsorption efficiency was 4 times as large as the adsorption efficiency of the culture container in Comparative Example 3 (12%).

As mentioned above, by producing a culture container by using the immobilizing apparatus of one or more embodiments of the present invention, a culture container that exhibits high adsorption efficiency that cannot be realized by conventional culture containers can be obtained.

The present invention is not limited to the above-mentioned embodiments or examples, and it is needless to say that various modifications are possible within the scope of the present invention.

For example, the size of a culture container, the type of lymphocytes, the type of a culture medium, the type of proteins, or the like can be appropriately changed such that they are different from those in the Examples.

INDUSTRIAL APPLICABILITY

One or more embodiments of the present invention can be preferably utilized for culturing a large amount of lymphocytes by using a single culture container while eliminating troublesomeness in transfer of activated cells or risk of contamination. In addition, one or more embodiments of the present invention can be preferably utilized for producing a culture container in which proteins are immobilized on the inner surface thereof efficiently for a short period of time.

EXPLANATION OF REFERENTIAL NUMERALS

10. Culture container
11. Immobilized surface
12. Non-immobilized surface
13. Tube
20. Antibodies
30. Lymphocytes
40. Culture liquid
50. Partitioning member
60. Outer covering container
70. Packaging container
100. Culture bag
110. Immobilized surface
120. Non-immobilized surface
130. Tube
200. Proteins
300. Immobilizing apparatus
310. Supporting table for moving in the X-axis direction
320. Supporting column
330. Servo motor for moving in the X-axis direction
340. Gear box for moving in the X-axis direction
350. Origin limit detection sensor for the Y axis
360. Supporting table for moving in the Y-axis direction
370. Servo motor for moving in the Y-axis direction
380. Gear box for moving in the Y-axis direction
390. Origin limit detection sensor for the X axis
400. Base stand
500. Retention member
510. Main body part
510-1. Recess part
520. Upper lid part
530. Pressing part

What is claimed is:

1. A culture bag for culturing lymphocytes, comprising:
   a first film member having gas permeability required for cell culture; and
   a second film member having gas permeability required for cell culture;
   wherein the first film member and the second film member are formed into bag-shape;
   a first surface inside the bag of the first film member is formed as an immobilized activating surface by immobilizing anti-CD3 antibodies at a concentration of 10 to 300 ng/cm2;
   a second surface inside the bag of the second film member is formed as a non-immobilized proliferating surface without immobilizing anti-CD3 antibodies; and
   a gas is sealed in an amount of 0.01 to 4 ml per cm$^2$ of a bottom surface area in the culture bag.

* * * * *